(12) United States Patent
Brenner et al.

(10) Patent No.: US 9,901,301 B2
(45) Date of Patent: Feb. 27, 2018

(54) COORDINATING RELATIONSHIP WEARABLES

(71) Applicant: eBay Inc., San Jose, CA (US)

(72) Inventors: Jennifer T. Brenner, Austin, TX (US); Bryant Genepang Luk, Round Rock, TX (US); Robert He, Pflugerville, TX (US); Christopher Diebold O'Toole, Cedar Park, TX (US); Yu Tang, Round Rock, TX (US); Jason Ziaja, Cedar Park, TX (US); Ananya Das, Austin, TX (US)

(73) Assignee: eBay Inc., San Jose, CA (US)

( * ) Notice: Subject to any disclaimer, the term of this patent is extended or adjusted under 35 U.S.C. 154(b) by 348 days.

(21) Appl. No.: 14/569,518

(22) Filed: Dec. 12, 2014

(65) Prior Publication Data

US 2016/0173359 A1 Jun. 16, 2016

(51) Int. Cl.
*G06F 17/30* (2006.01)
*A61B 5/00* (2006.01)
(Continued)

(52) U.S. Cl.
CPC .......... *A61B 5/6801* (2013.01); *A61B 5/0022* (2013.01); *A61B 5/0205* (2013.01);
(Continued)

(58) Field of Classification Search
CPC ................. H04L 43/16; G06F 17/3051; G06F 17/30598; A61B 5/0205; A61B 5/6801; A61B 5/02438
See application file for complete search history.

(56) References Cited

U.S. PATENT DOCUMENTS

| 5,544,355 A | 8/1996 | Chaudhuri et al. |
| 8,811,951 B1 * | 8/2014 | Faaborg .................. H04M 1/57 340/384.1 |

(Continued)

FOREIGN PATENT DOCUMENTS

| WO | WO 2012061438 A2 * | 5/2012 | ............. A61B 5/681 |
| WO | WO-2012061438 A2 | 5/2012 | |
| WO | WO-2016094623 A1 | 6/2016 | |

OTHER PUBLICATIONS

"International Application Serial No. PCT/US2015/064928, International Search Report dated Feb. 5, 2016", 2 pgs.

(Continued)

*Primary Examiner* — Anil Bhargava
(74) *Attorney, Agent, or Firm* — Schwegman Lundberg & Woessner, P.A.

(57) ABSTRACT

In various example embodiments, devices including a wearable device may be associated to share information and coordinate data between the devices as part of a coordination between relationship wearables. For example, a first wearable device and a second device, each associated with different users, may provide data to a history analysis module. The history analysis module may analyze this data for coordinated relationship patters made up of repeated events. Coordinated relationship data may be generated by this analysis, and then used by a current data analysis module to analyze an incoming stream of current data from at least one of the devices. When a repeated status value is identified within the current data stream, a coordination communication may be initiated.

20 Claims, 11 Drawing Sheets

(51) Int. Cl.
*A61B 5/0205* (2006.01)
*A61B 5/024* (2006.01)
*G06F 19/00* (2018.01)
*H04L 29/08* (2006.01)
*A61B 5/01* (2006.01)
*A61B 5/021* (2006.01)
*A61B 5/11* (2006.01)
*A61B 5/1172* (2016.01)

(52) U.S. Cl.
CPC .......... *A61B 5/02438* (2013.01); *G06F 19/00* (2013.01); *G06F 19/3406* (2013.01); *G06F 19/3418* (2013.01); *H04L 67/00* (2013.01); *H04L 67/12* (2013.01); *A61B 5/01* (2013.01); *A61B 5/021* (2013.01); *A61B 5/1112* (2013.01); *A61B 5/1172* (2013.01); *A61B 5/681* (2013.01); *A61B 5/6823* (2013.01); *A61B 5/6824* (2013.01); *A61B 5/7275* (2013.01); *A61B 5/7282* (2013.01); *A61B 2562/0219* (2013.01)

(56) References Cited

U.S. PATENT DOCUMENTS

| | | |
|---|---|---|
| 9,348,895 B2 | 5/2016 | Bao et al. |
| 9,626,430 B2 | 4/2017 | Kumar et al. |
| 2009/0069642 A1* | 3/2009 | Gao .................. A61B 5/02055 600/300 |
| 2009/0198644 A1 | 8/2009 | Buchner et al. |
| 2009/0216710 A1 | 8/2009 | Chang et al. |
| 2013/0176142 A1* | 7/2013 | Drysdale ................. G06F 3/011 340/870.02 |
| 2013/0246449 A1 | 9/2013 | Balannik et al. |
| 2013/0262350 A1 | 10/2013 | Garg et al. |
| 2013/0262351 A1 | 10/2013 | Garg et al. |
| 2013/0290427 A1 | 10/2013 | Proud |
| 2014/0052567 A1 | 2/2014 | Bhardwaj et al. |
| 2014/0073969 A1 | 3/2014 | Zou et al. |
| 2014/0130076 A1* | 5/2014 | Moore ............. H04N 21/25883 725/19 |
| 2014/0142403 A1* | 5/2014 | Brumback ......... A61B 5/02433 600/324 |
| 2014/0236847 A1* | 8/2014 | Hamilton ........... G06Q 10/1093 705/319 |
| 2014/0275854 A1* | 9/2014 | Venkatraman ......... A61B 5/721 600/301 |
| 2014/0343380 A1 | 11/2014 | Carter et al. |
| 2016/0179807 A1 | 6/2016 | Kumar et al. |
| 2017/0206280 A1 | 7/2017 | Kumar et al. |

OTHER PUBLICATIONS

"International Application Serial No. PCT/US2015/064928, Written Opinion dated Feb. 5, 2016", 12 pgs.

"U.S. Appl. No. 14/579,946, Notice of Allowance dated Dec. 9, 2016", 9 pgs.

"U.S. Appl. No. 15/474,560, Preliminary Amendment filed May 25, 2017", 9 pgs.

"European Application Serial No. 15868461.3 Response filed Jul. 26, 2017 to Communication pursuant to Rules 161(2) and 162 EPC", 17 pgs.

"International Application Serial No. PCT/US2015/064928, International Preliminary Report on Patentability dated Jun. 22, 2017", 14 pgs.

* cited by examiner

COORDINATING RELATIONSHIP WEARABLES

TECHNICAL FIELD

Embodiments of the present disclosure relate generally to wearable electronics, and, more particularly, to a coordinating data between multiple devices.

BACKGROUND

Wearable devices include small electronic systems with sensors and other inputs that meet be used together information about a wearer. Watches, bracelets, armbands, and other such wearable items may be integrated with electronic components and sensors as part of a user's clothing or worn accessory. Many such devices exist to provide information to the wearer and about the wearer from an individual device. Embodiments described herein include improved systems and methods for managing multiple wearable devices for multiple users in a coordinated fashion.

BRIEF DESCRIPTION OF THE DRAWINGS

Various ones of the appended drawings merely illustrate example embodiments of the present disclosure and cannot be considered as limiting its scope.

Figure 1A:
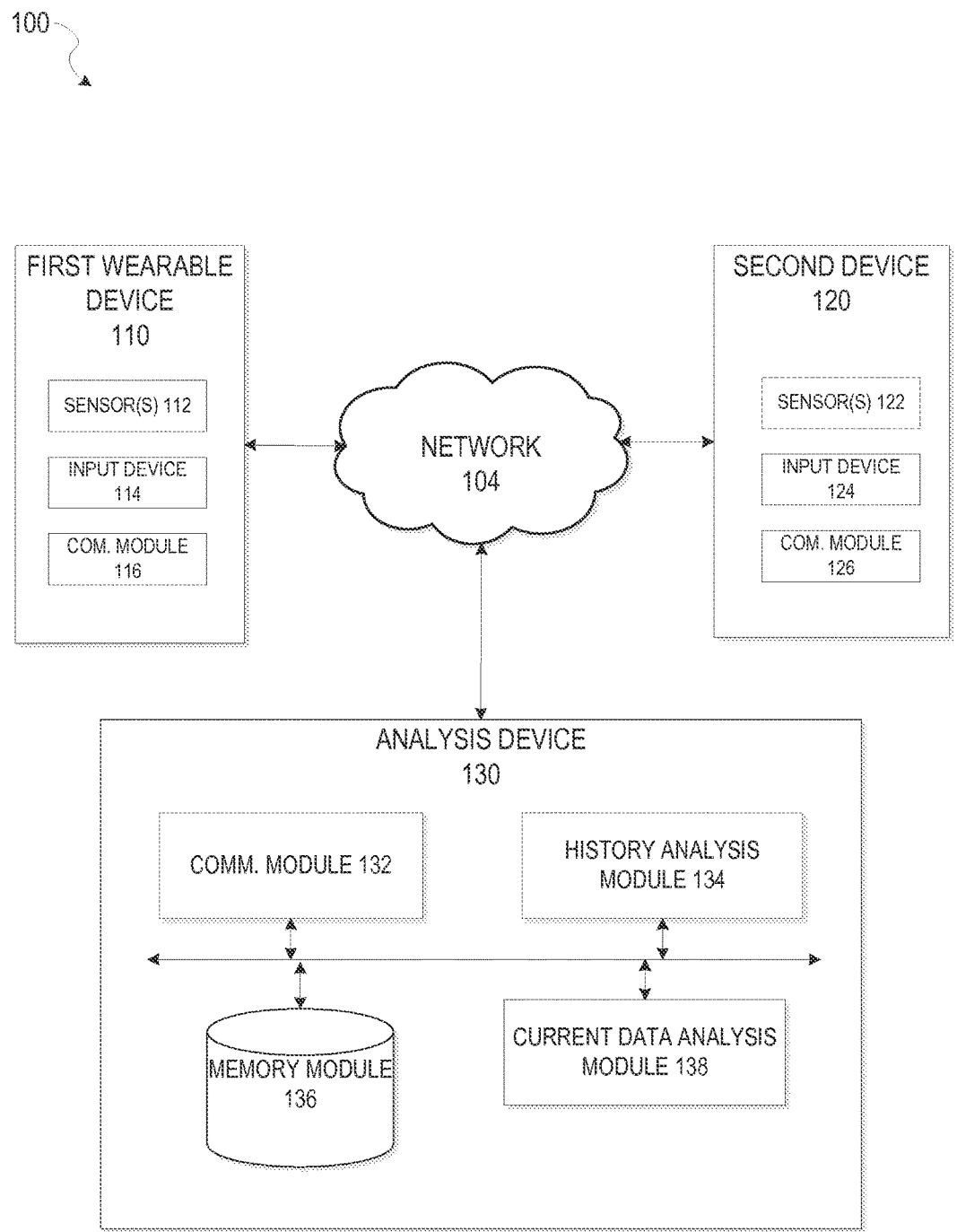
FIG. 1A illustrates system for coordinated relationship wearables according to one example embodiment.

The headings provided herein are merely for convenience and do not necessarily affect the scope or meaning of the terms used.

DETAILED DESCRIPTION

The description that follows includes systems, methods, techniques, instruction sequences, and computing machine program products that embody illustrative embodiments of the disclosure. In the following description, for the purposes of explanation, numerous specific details are set forth in order to provide an understanding of various embodiments of the inventive subject matter. It will be evident, however, to those skilled in the art, that embodiments of the inventive subject matter may be practiced without these specific details. In general, well-known instruction instances, protocols, structures, and techniques are not necessarily shown in detail.

This description relates to devices, systems, and methods associated with wearable electronics, and, more particularly, to coordinating data between a wearable device and another device based on an identified relationship between the devices. For example, two people may each wear wearable devices such as rings, bracelets, or watches. Each of these wearable devices may generate biometric data. A system for coordinating relationship wearables may collect this biometric data and integrate this data with other history data such as social media data. This history data may be analyzed to identify patterns. The identification of such patterns may be assisted by inputs from one or both of the users, or may be based on system options or models. Once patterns are identified using the history data, current streams of biometric data or other data may be sent to the system. This data stream may be analyzed for indicators that an event from the repeated pattern is occurring. Once an indicator that the pattern is occurring is identified by the system, the system may initiate a communication to one or both of the system users associated with the devices.

In a specific example, a first user may wear a bracelet that includes a heart rate sensor. A set of history data may include heart rate measurements from the heart rate sensor as well as information from a social media network site, inputs from a second user's device identifying a relationship state, images of a user's face, or any other such data associated with the user or the context in which the user is operating. As the system gathers more and more history data, patterns may be identifiable within the history data. For example, one identifiable event that occurs regularly at a certain day and time may be associated with a particular set of data.

Data for a the first user may particularly include (1) the first user's wearable device providing GPS position data identifying the user as being a driver in a car, (2) the heart rate sensor data identifying that the user's heart rate is elevated for an extended period of time while driving, and (3) calendar data identifying the date and time as between 6 and 8 PM on a Monday. Data for a second user that has been associated with the first user by a system registration may independently generate a user input or social media data indicating that between 7 and 8:30 PM on the same date associated with the event data above, the second user input to a mood category value indicating that the first user was exhibiting high tension and stress levels.

A system for coordinating relationship wearables may analyze a set of history data to determine that the above event identified by this data repeats with an identifiable level of regularity. The system may flag this pattern of repeated events as a coordinated relationship pattern between the users. As the system continues to gather data including near real-time streams of data from the wearable device or other similar such streams of data, the system may identify values from the repeated event which may be used as to predict that the event is occurring in the predictably repeated fashion. These values may be used to generate a trigger threshold. The trigger threshold may be compared against incoming data, and when a portion of the incoming data meets the trigger threshold, the system may initiate a coordination communication to either or both users. This communication may simply notify the users that the system is predicting an additional event from the coordinated relationship pattern.

The communication may additionally or alternatively initiate any action selected by either or both users. For example, the second user may input a system setting so that the coordination communication may initiate an automatic purchase that was preselected by a second user. In the specific example above, when the system receives current data indicating the users position in a car combined with the date, time, and threshold heart rate levels, this identification of the trigger may automatically communicate a food delivery purchase message with payment and a request for delivery at within 30 minutes.

As described herein a "repeated status value" refers to a portion of a data stream or a set of device data from a wearable device which is associated with a repeated event and which is used by a history analysis module to generate a trigger threshold. A "coordinated status value" refers to a portion of a data stream or a set of device data associated with the same repeated event as the repeated status value, but the coordinated status value is not used to generate the trigger threshold. A "trigger threshold" refers to a value or a window or set of values which may be compared against a current data stream to identify a portion of the current data stream that is sufficiently similar to the repeated status value to be used as an indication that an instance of the repeated event is occurring. In the example above, any of the position data (indicating the user is in the car), time data (indicating when the user is in the car), and heart rate data (indicating a high heart rate) may be part of a repeated status value. The social network data or user input data from a second user may be part of a coordinated status value indicating a stressed state for the user. The trigger threshold may be a range of values associated with each element of the repeated status value, such as (threshold position=in car; threshold time=Monday 6-8 PM; threshold heart rate=100-160 BPM.)

Figure 1B:
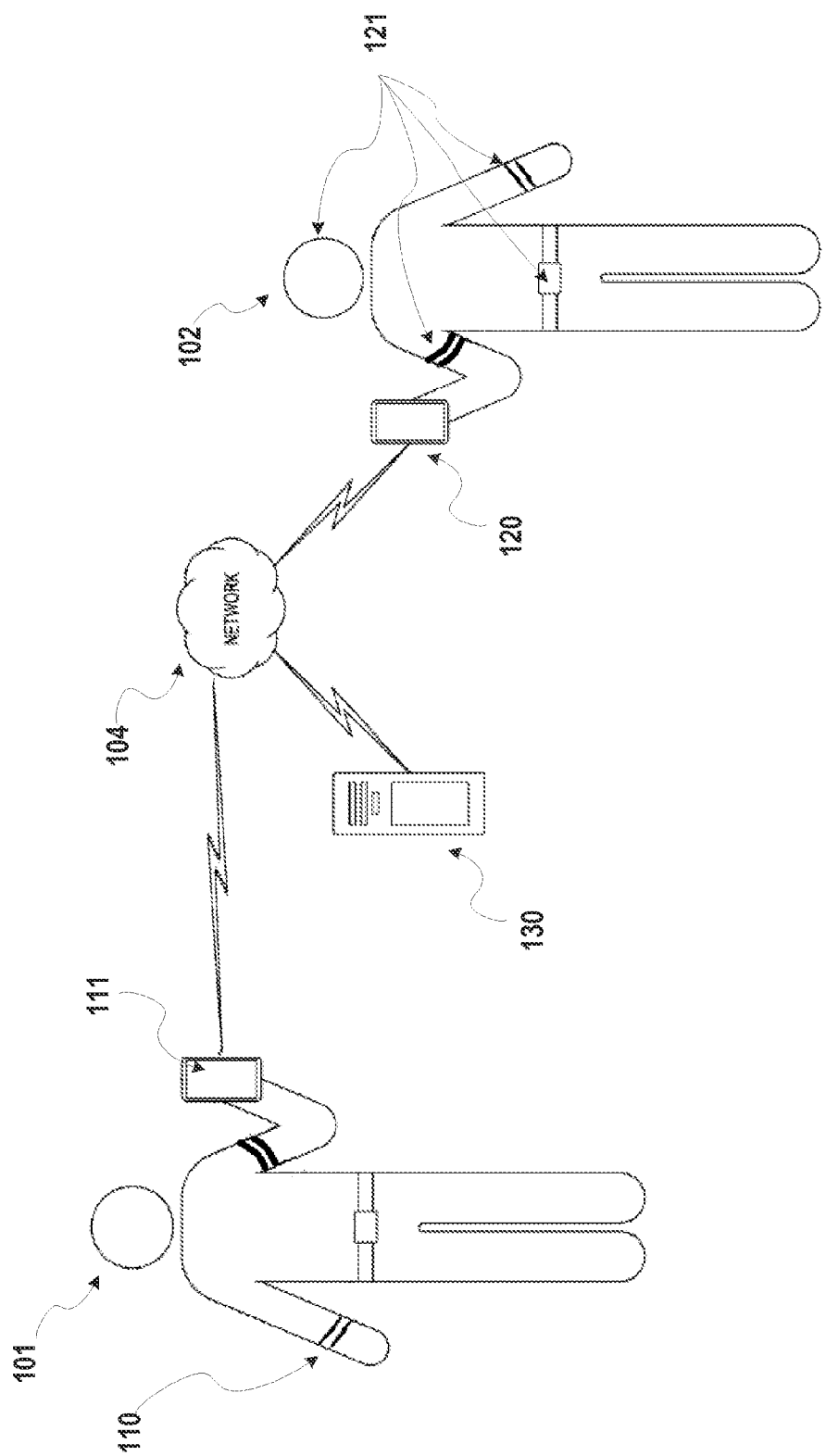
FIG. 1B illustrates additional aspects of a system for coordinated relationship wearables according to one example embodiment.

FIG. 1A illustrates a block diagram of one embodiment of a system 100 for coordinating relationship wearables. 1B illustrates additional aspects of system 100. Such a system may operate to identify patterns, identifying triggers in current data predicting a repetition of an event in the pattern, and initiate a coordination communication in response to identification of such a trigger. System 100 as illustrated by FIG. 1A includes a first wearable device 110 a second device 120 and an analysis device 130. As part of system 100 operation, first wearable device 110, second device 120, and analysis device 130 communicate via network 104. FIG. 1B shows additional elements of a first user 101, a second user 102, a first user mobile device 111, and a plurality of second user wearable devices 121.

Network 104 may be a wide area network such as the Internet, a local area network implemented with a single wireless access point, a wired network, a cellular communication network, or any other such network that may enable communication between devices.

First wearable device 110 is illustrated in FIG. 1B as a wearable wristband. In other embodiments, first wearable device 110 may be similar to any of a plurality of second user wearable devices 121, which may include a wristband, a watch, a belt, a pair of eyeglasses, a headset, and armband, or any other such wearable device with integrated electronics including sensors 112, input device 114, and communication module 116. Any such wearable devices may be similar to FIG. 1B further shows the first wearable device 110 communicating with network 104 via first user mobile device 111. In other embodiments, first wearable device 110 may communicate directly with network 104 without the assistance of an intermediate mobile device. In certain embodiments of the first wearable device 110, input device 114 and communication module 116 may be part of the same module. In such embodiments, the only control input to first wearable device 110 may be a wireless communication module 116 having a communication input. In other embodiments, input device 114 may be a mechanical button, a touchscreen interface, or any other such input mechanism described herein. Sensors 112 may include heart rate monitors, blood pressure monitors, camera elements, position measuring the elements, gyroscopes, accelerometers, or any other such sensor element. Additional embodiments of sensors are described below with respect to FIG. 8. In certain embodiments, communication module 116 may be integrated with one or more sensors 112. For example, in certain embodiments and network storage may independently send and receive information for a particular sensor 112. Additionally, in certain embodiments, first wearable device 110 may include a processor that receives information from a separate source such as a social media network fire communication module 116. This information may then be sent out from first wearable device 110 as part of device data or in separate data streams alongside other sensor data from sensors 112.

Second device 120 may be, in certain embodiments, a wearable device including any device described for first wearable device 110. In certain particular embodiments, first wearable device 110 and second device 120 may each be smart phone devices with integrated sensors. Second device 120 is shown in FIG. 1B as acting as an interface for other wearable devices 121. In other embodiments, second device 120 may operate without any other wearable devices 121 using second device 120 to access network 104. In other embodiments, second device 120 may simply be a computing device such as a desktop computer, a tablet computer, a laptop computer, or any other such computing device. Second device 120 includes input device 124 and communication module 126. Certain implementations of second device 120 may optionally include sensors 122 similar to sensors 112 described above. In embodiments of second device 120 without any sensors 122, the coordinated data provided to a system as history data from second device may simply be data inputs provided by a keyboard or a user interface to menu and input to the system as a coordinated data stream from a second user that is associated with a first user and the first wearable device 110.

Analysis device 130 includes communication module 132, memory module 136, history analysis module 134, and current data analysis module 138. Communication module 132 may be any hardware, software, or firmware module that enables communication with first wearable device 110 and second device 120 via network 104. In certain embodiments, analysis device 130 is a network server computer. In other embodiments, analysis device 130 may be a virtual computing module implemented on a network server computer that shares hardware resources with other unrelated systems. In still further embodiments, analysis device 130 may be a distributed system implemented across multiple server computer systems. For embodiments where network 104 is a local area network, analysis device 130 may be a desktop computer or laptop computer.

History analysis module 134 and current data analysis 138 may operate as hardware, software, or firmware modules operating on any such device. History analysis module 134 gathers sensor data from sensors 112 as well as other data from a variety of different sources that may be selected by users of first wearable device 110 and second device 120. This includes input data from input device 114, input data from input device 124, and relayed information from any source. This data may be received at the appropriate analysis module from a communication module 116 or communication module 126. In certain embodiments, analysis device 130 may further be communicatively coupled to other server computers including web servers and web databases that may provide data to analysis device 130. Such data may be selected by a user of first wearable device 110 or second device 120 and communicated as a configuration selection to analysis device 130.

As history analysis module 134 receives data, it processes this data using various machine learning algorithms or pattern recognition algorithms to identify patterns within the data from the two devices. In certain embodiments, this may include unsupervised training which does not use any additional data sets to identify patterns within the history data but simply searches for repeated strings of values that occur within the history data. This may include the use of clustering models, Markov models, structured prediction models, or any other such model for identifying an event that is repeated as part of a coordinated relationship pattern.

In other embodiments, this pattern identification may include supervised training models which use sets of training data to recognition patterns within history data. In such embodiments, history analysis module 134 may identify the types of data that are being received as history data. In one embodiment, a registration of a first user and the second user with system accounts may include a device set up which involves the users selecting data types to be provided to the system. For example, a user may select heart rate data, but not position data, to be provided to the system. Additionally, in conjunction with user selecting data types, a user may select coordination types as a focus for the coordination of the relationship wearables. For example, users may select a focus on stress patterns. The user configuration inputs selecting data types and pattern types may be used by a pattern recognition system to select pattern recognition models and training data sets that may be used to identify patterns within the history data for the first and second users. The system may use these configuration selections to identify the individual events that repeat within a pattern associated with the type of pattern selected by the users. This may further be used to identify trigger values within history data that predictably occur with each event. This may include triggers which are not observable by the users. For example, when both users provide wristband motion data and heart rate data to the system, the history data may associate certain nighttime sleep movement patters for both wearable devices with a daytime elevated heart rates for both users. Once an initial model has completed development of an initial set of triggers, current streams of data analyzed for the triggers may also be used to update the history data, and the models may continue to update training data and triggers generated by the supervised training models.

Once models and analysis types are selected, either by the system alone or with user configuration selections, the history analysis module 134 may process the received history data using the models and to identify coordinated relationship patterns. This may also include the generation of a set of coordinated relationship data that identifies repeated status values within history data. Subsets of coordinated relationship data may then be stored in memory module 136. In certain embodiments, coordinated relationship data may be stored alone with history data that is only from devices associated with a first and second user. In other embodiments, a database may include sets of coordinated relationship data for any number of users and devices.

For example a first user may register a first account and associate a first set of wearable devices including first wearable device 110 with the first account a second user may do the same with devices including second device 120. The first and second user may then associate their accounts and select configuration inputs which initiate a coordinating of relationship wearables for devices associated with the users. History data may then be generated from the devices of the two users and analyzed to generate coordinated relationship data. At the same time, a third user may register an account with a third set of devices. The first user may also create an association with the third user and the devices of the third user. History analysis module 134 may additionally analyze a second set of history information including information from devices of the first user and information from devices of the third user. History analysis module 134 may perform the same analysis on the second set of history data as was performed for the first set of history data. This analysis may be based on user selections which may be the same or different for different associations between users and user devices. In certain embodiments, such a first association between the first and second user may include selection of heart rate and position data. A second association between the first user the third user may include selection of position data but not heart rate data. Different models may then be used to analyze the different sets of history data which result from these user selections. The different sets of coordinated relationship data for each pair of users may then be stored in memory module 136.

In additional embodiments, more complex associations including associations of three users, four users, or any number of users may be generated by the system or selected as part of a user registration. History analysis module 134 may then use different analysis models and techniques to identify patterns within these more complex associations. This may include history data from sensors, user inputs, and other data sources associated with users in an association group. Additional details associated with history data that may be analyzed by history analysis module 134 are particularly discussed below with respect to FIGS. 2 and 5.

Current data analysis module 138, similar to history analysis module 134 may operate as hardware, software, firmware, or any combination of these. Current data analysis module 138 receives a current data stream from first wearable device 110. This data stream may be coupled with data from other sources, either at first wearable device 110 or at analysis device 130. Current data analysis module 138 identifies trigger values, also referred to herein as repeated status values, which are associated with an event that has been identified as part of a coordinated relationship pattern by history analysis module 134. In certain embodiments, a current data stream includes multiple data sets that are received separately. For example, each set may include all device data generated over a five minute time period with an analysis device 130 receiving a new set of data as part of the current data stream every five minutes. This may include, for example, multiple heart rate measurements taken over the time period. In alternate embodiments, individual measurements may be communicated to the current data analysis module 138 as each measurement or piece of data is created. In such embodiments, current data analysis module 138 may receive individual heart rate measurements at unpredictable times. In other embodiments, combinations of such data may be used in the current data stream received at current data analysis module 138. Information received in the current data stream need not be real-time data. Certain embodiments may, however, include a time check to verify that the data is sufficiently recent within system parameters to be relevant to the generation of a coordination communication. Different user coordination events or patterns may have different time thresholds for determining relevancy. For example, one coordinated relationship pattern and associated events may require that data associated with a trigger threshold have occurred within a time threshold of 30 seconds, while a second different pattern with different events and trigger thresholds may have a time threshold of 10 minutes.

In embodiments where the current data analysis module receives a stream of current data, and none of the data is sufficiently current given relevancy timing thresholds, then the current data may simply be passed to the history analysis module 134 for processing and to update the history data and any identified patterns or events related to the users that generated the current data stream. Similarly, if the current data stream is analyzed by current data analysis module 138 and no triggers are identified, then the information in the current data stream may be passed to history analysis module 134 for processing.

In a current data stream where a trigger is identified by current data analysis module 138, such a trigger may be identified in a variety of different ways. In certain embodiments, when a user registers for a system and selects device and data types to be provided to the system, the system may automatically present trigger options associated with the type of data or type of device. For example, if heart rate data is selected based on a user's indication that a heart rate monitor will be providing data to coordinate relationship wearables, each user associated with a heart rate monitor may provide baseline heart rate measurement values. These values may be associated with a resting heart rate and various levels of exercise. In other embodiments, the system may request a training process, where the wearables are worn, and send a stream of current data to current data analysis module 138 along with user input device data providing standardized descriptions of the user's activity that can be associated with the data stream. In other embodiments, standardized values derived from registration information such as a user's age, weight, or other details may be used to generate a default set of target thresholds. Such target thresholds may then be adjusted using history data in a feedback loop with user feedback or automatic system feedback at any point during system operation. Just as described above for pattern recognition with history analysis module 134, the adjustment to threshold values may use a trained or untrained model to adjust values or value windows of trigger thresholds. Trained models may use history data not only from the user associated with a trigger threshold, but also for users with similar profiles or data types.

As detailed above, a trigger threshold may identify any value which may be associated with a relationship pattern. Elaborating on the initial example with heart rate data, a trigger threshold may involve a user's heart rate in a window between 100 and 160 beats per minute over a period of 5 minutes. Such a trigger threshold may also include any number of other trigger components, such as this heart rate occurring between 6 PM and 8 PM on a weekday when a location service identifies the wearable as moving at automobile speeds along freeway streets when a calendar identifies a certain type of meeting as having occurred during the day. Such a trigger threshold may thus involve data from multiple sensors and data sources. Similarly, the trigger threshold may involve sensors from multiple devices, including a first device associated with a first user and a second device associated with a second user, where the two devices have a coordinated relationship association established. In such embodiments, the above trigger threshold may also involve elements associated with the second device, such as a device location, a heart rate window for the second user, a recent social media update made on an account associated with the first or second user, or any other such threshold that may be associated with this data. As information in the current data stream is received by current data analysis module 138, the information in the current data stream may be ordered and associated with a data source. The ordered and identified elements of the current data stream mailing can be compared with any number of trigger thresholds to identify a match.

When a repeated status value is identified by current data analysis module 138, the current data analysis module 138 initiates a coordination communication. This coordination communication may then be communicated by communication module 132 to second device 120, first wearable device 110, both, or any other device. In certain embodiments, the coordination communication may simply list the repeated status value which was identified in the current data stream. The coordination communication may additionally list the trigger threshold which was used to identify the repeated status value. In certain embodiments, a pre-generated message may be sent which is based on the trigger threshold. For example, any data stream values with element values within a window of a particular trigger threshold may initiate a communication with the same message content, such that a current data stream indicating a heart rate of 110 beats per minute may generate the same message as a current data stream indicating ahead rate of 120 beats per minute.

In certain embodiments, the current data stream values identified using the trigger threshold may not have a perfect association with the expected event and the coordinated relationship pattern that is a pattern of the event repeating identified by the history analysis module. In certain embodiments, the history analysis module may quantify a statistical association between instances of a portion of a current data stream meeting the trigger threshold and the occurrence of the event that is part of the coordinated relationship pattern. In such embodiments, the coordination communication may include such statistical information along with any other content.

In certain embodiments, a system may have multiple different trigger thresholds associated with a coordinated relationship pattern. In such an embodiment, the different trigger thresholds may share certain elements, but may have different statistical associations with the expectation of the event actually occurring. For example, a first trigger threshold may have a heart rate element and a time element. A second trigger threshold may have the heart rate element, the time element, and a location element. If the first trigger threshold is used to identify a first repeated status value where a position associated with the first repeated status value is outside the value of the position element of the second trigger threshold, then a first coordination communication may be sent. If, as the wearable device's position changes, and the position identified by the current content data stream moves into the threshold range for the position threshold element of the second trigger value while all other elements of the second trigger threshold are met, then a second different coordination communication may be sent. Similarly, a system may have multiple different trigger thresholds associated with different ranges of a data type. For example, if current data analysis module 138 receives a current data stream with heart rate data indicating 110 bpm, then first trigger threshold may be used to initiate a first coordination communication to a second user. If, however, a current data analysis module 138 receives a current data stream with heart rate data indicating 200 beats per minute, then a second trigger threshold may identify an emergency status value which is used to initiate a second coordination communication to the second user and an emergency communication to a medical service. In such an embodiment, a current data analysis module 138 receiving the current data stream with a heart rate indicating 50 beats per minute and a particular position and movement pattern may be used to send a third different message to the second user, tier example indicating that the first user is sleeping.

In additional alternative embodiments, analysis device 130 may include a separate optional reporting module, or reporting functionality may be integrated with history analysis module 134. In such embodiments, in addition to analysis device 130 generating and communicating coordination communications, reports may be generated identifying any coordinated relationship patterns from history analysis module 134, any trigger thresholds input by a user or generated by a system model, any statistical associations between various trigger thresholds and coordinated relationship patterns, details of any coordination communication sent by a system, details of any user accessing any coordinated relationship data stored by the system, or any other such system details.

Figure 2:
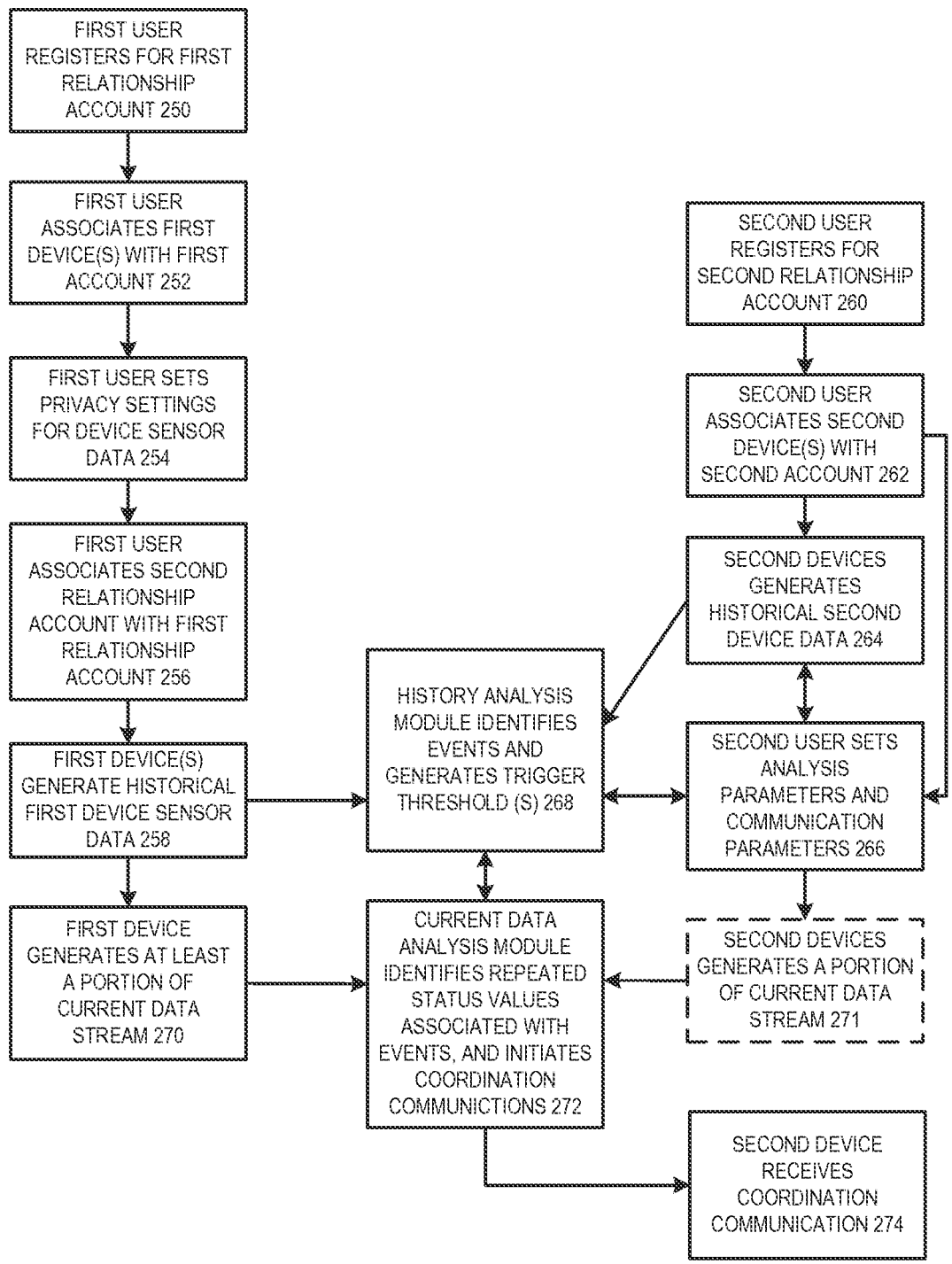
FIG. 2 is a flowchart illustrating aspects of a method of coordinating relationship wearables according to some example embodiments.

FIG. 2 illustrates a flowchart showing aspects of coordinating relationship wearables according to certain example embodiments. For the purposes of illustration, FIG. 200 is described with respect to system 100 of FIGS. 1A and 1B. In alternative implementations, the operations of FIG. 2 may be implemented in any other system which may be used for coordinating relationship wearables as described herein.

In operation 250, first user 101 registers for a first relationship account associated with analysis device 130. Such a registration process may involve the first user 101 providing personal details which may be used by analysis device 130 as part of coordinating relationship wearables. After an initial registration in operation 250, in operation 252 the first user 101 associates one or more first devices with the first account. This may include the first wearable device 110 as well as first user mobile device 111 and any other computing devices which may be used by user 101 in conjunction with the first relationship account.

In operation 254, first user 101 sets privacy settings for device data including sensor 112 data and any other such sensor data that may be created by devices associated with the first relationship account in operation 252. In operation 256, the first user associates a second relationship account with the first relationship account. This process may involve simply adding the user ID for the second relationship account to an authorization list associated with the first relationship account. This may also involve additional privacy authentication between both the first relationship account and the second relationship account. In additional registration or user configuration processes, first user 101 may additionally provide threshold settings which are used to identify certain repeated relationship patterns, and to identify events within these patterns. Such threshold settings may particularly be used when another user such as second user 102 settings in a second relationship account that provide the first user account with access to sensor data or other data generated by devices associated with a second relationship account. Such threshold settings may be used to generate coordination communications which are targeted for the first user 101.

After all initial registration and user customization settings are received by system, then in operation 258, the first user 101 operates devices including the first wearable device 110 and generates historical first device into data. This initial historical first device center data may be distinguished from later streams of current first device data in that the system has yet to generate models, identify repeated relationship patterns, and/or generate threshold triggers. In various embodiments, a threshold trigger may be a complex variable, pattern, model, or other such comparison tool other than a simple threshold value or threshold window. In certain embodiments, a trigger threshold may be a threshold value associated with a weighted variable using elements of a repeated status value. Such patterns and associated events are identified by a system and used to generate such threshold triggers in operation 268. As described above, history analysis module 134 may be used to analyze historical data and to identify events, repeated status values, coordinated status values, and other aspects of a coordinated relationship pattern made up of repeated events. As part of coordinating relationship wearables, operation 268 includes data not only from devices such as first wearable device 110 associated with the first relationship account, but also includes data from one or more devices such as second device 120 which are associated with a second relationship account.

As part of enabling data from devices associated with the second relationship account, operations 260 through 266 include registration and user selection inputs for the second relationship account similar to those described above for the first relationship account. Operation 260 involves creation of the second relationship account. Operation 262 involves association between the second user account and one or more second devices such as second device 120. Operation 264 involves generation of historical second device status similar to be historical data discussed just previously. In certain embodiments, the second relationship account may not provide the first user account with visibility or access to the historical second device data. In other embodiments, the coordination between the first relationship account and second relationship account may be symmetrical, and the second user may set privacy settings to associate a second relationship account with the first relationship account and enable the first user to receive coordinated communications based on historical second device data.

In operation 266, the second user sets analysis parameters and communication parameters. Such analysis parameters may simply include default system trigger thresholds which are used to identify events which are then used to identify the coordinated relationship pattern. Such default system trigger thresholds may be set based on input sensor types or other data types along with user input selections, and then modified in response to the analysis of history analysis module 134. In other embodiments, this may include selection of provided data types from the first user account, selection of different models available on the system, selection of system templates which may be used to identify standardized types of coordinated relationship patterns, or any other such system settings available to the second user has been provided with access to information from the first relationship account by the privacy settings of operation 252 and the association created in operation 256.

In various alternative embodiments, certain analysis parameters and communication parameters may be generated prior to any generation of second historical device data.

In the embodiment of FIG. 2, a second user 102 may review a set of coordinated relationship data generated by history analysis module 134 prior to finalizing analysis parameters and communication parameters that are used, at least in part, to set trigger thresholds which define events and repeated status values of a coordinated relationship pattern.

Once all historical data from first wearable device 110, second device 120, and any other devices associated with the first or second relationship account are provided to history analysis module 134, history analysis module 134 may generate final models for coordinated relationship patterns and generate trigger thresholds, and may activate current data analysis module 138 to analyze streams of data being received from the first wearable device 110, the second device 120, or any other device associated with the first relationship account with a second relationship account.

Then, in operation 270, the first device generates a current data stream. This current data stream may be identical to the historical first device into data, or may be customized to be different from the historical first device data. For example, historical first device data may include additional metadata or configuration data which is used to generate models or identify patterns by history analysis module 134. This data may be eliminated from the current data stream of operation 270 in order to optimize regular system operation. As part of such operation, data generated as historical second device data in operation 264 may be optional as part of operation 271 where a portion of the current data stream may be generated by the second devices. Additionally, while certain embodiments may involve generation of a current stream of data from devices associated with both the first relationship account and the second relationship account, other embodiments including operation 270 of FIG. 2, only include data from the first wearable device 110 or other devices or networked resources generating data associated with the first user 101. In such embodiments the coordination of relationship wearables between the first relationship account in a second relationship account occurs during the analysis performed by historical analysis module 134, and the analysis of current data analysis module 138 may use information from a single users devices in order to predict an event that is part of a coordinated relationship pattern. Thus, in operation 272, current data analysis module 138 receives the current data stream at least in part from first wearable device 110. Current data analysis module 138 uses this current data stream from first wearable device 110 to identify portions of a current data stream that meet the trigger threshold associated with events, and to initiate coordinated communication with second device 120 when the trigger threshold is met. Following this, in operation 274, second device 120 receives the coordinated communication. The coordinated communication may enable additional automated actions as part of coordinating relationship wearables such as automated communications with first user 101, updating of data device 120, third party communications, system alerts or alarms, or other such similar actions.

Figure 3:
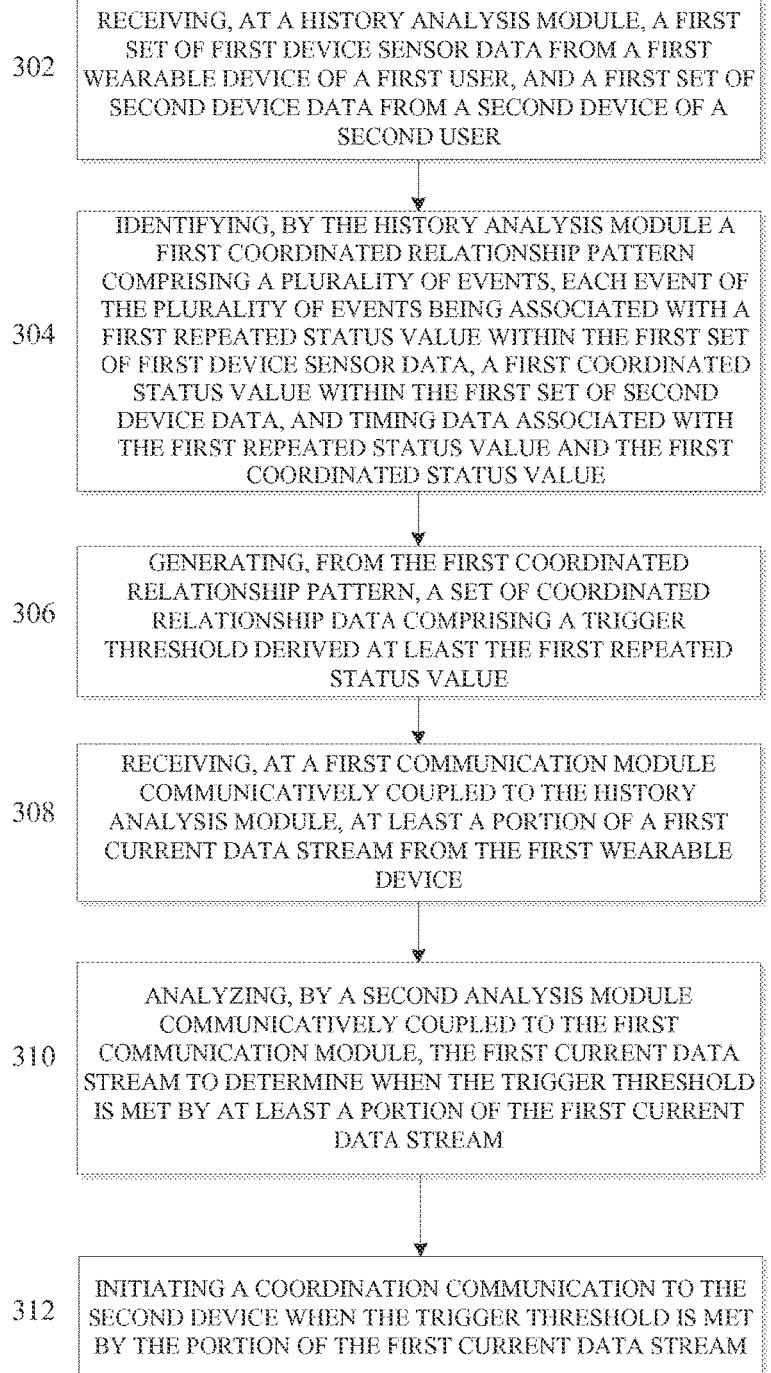
FIG. 3 illustrates a method of coordinating relationship wearables according to some example embodiments.

FIG. 3 then illustrates an additional method shown as method 300 for coordinating relationship wearables in accordance with certain example embodiments. While various different systems and devices may be used to implement method 300, for the purposes of illustration, method 300 is described here with respect to system 100. Additionally, while method 300 is one example embodiments, additional alternative methods may be used to implement coordination between relationship wearables in accordance with different embodiments.

Operation 302 of method 300 includes receiving, at a history analysis module 134, a first set of first device sensor data from first wearable device 110 of the first user, and a first set of second device data from second device 120 of the second user.

Operation 304 includes identifying, by the history analysis module 134, a first coordinated relationship pattern. As described above, a coordinated relationship pattern comprises a plurality of events. This may include a single type of repeated event, or multiple different repeated events that generate the pattern. Each event of the plurality of events is associated with a first repeated status value within the first set of first device sensor data. Each of the plurality of events is also associated with a first coordinated status value within the first set of second device data. Finally, each event is associated with timing data that may be used to relate the first repeated status value from the first device and the first coordinated status value from the second device. Such an event repeated in a coordinated relationship pattern describes a simple coordinated relationship pattern.

Additional embodiments of a coordinated relationship pattern may have a first event, a second of it, or any number of events, with each event type within the pattern having different repeated status values or other differences between the event types. As described above, trigger is associated with such different event types may have different statistical correlations with a coordinated relationship pattern.

Operation 306 then includes generating, from the first coordinated relationship pattern identified by the history analysis module 134, a set of coordinated relationship data comprising at least a trigger threshold. As described above, while in certain embodiments, a trigger threshold may be a simple number and data type, in other embodiments, a repeated status value may be a complex set of many different data type values, data flags, or other such information which may be combined into a set as a repeated status value.

Operation 308 includes receiving, at a first communication module 132 that is communicatively coupled to the first analysis module 134, at least a portion of a first current data stream from the first wearable device 110. As discussed above, a current data stream such as the first current data stream may include data from one or more sensors 112 of a first wearable device 110, and may additionally include data from other sources such as a social network server computer, independently network sensors in addition to sensors 112 first wearable device 110, or any other such source of data that may be integrated with a current data stream. In certain embodiments, the first current data stream may include data from second device 120 including measurements from sensors 122, other wearable devices coupled to a second device 120, or data from a memory or input device 124 of second device 120 communicated via communication module 126. In other embodiments, a second separate current data stream may be sent independently by second device 120. The data stream from second device 120 may be structured as a separate current data stream so that the data from second device 120 may be independently associated with other devices such as a third device, a fourth device or any number of other devices that may have separate coordinated wearable relationships with second device 120. A data stream from first wearable device 110 may be kept separate and independent for similar reasons. For the purposes of operation 308, any such data streams are considered to be integrated as part of the first current data stream.

Operation 310 includes analyzing, by a second analysis module 138 that is communicatively coupled to the first communication module 134, the first current data stream using the trigger threshold. Operation 312 includes initiating a coordination communication to the second device 120 when the trigger threshold is met by a portion of the first current data stream.

Figure 4:
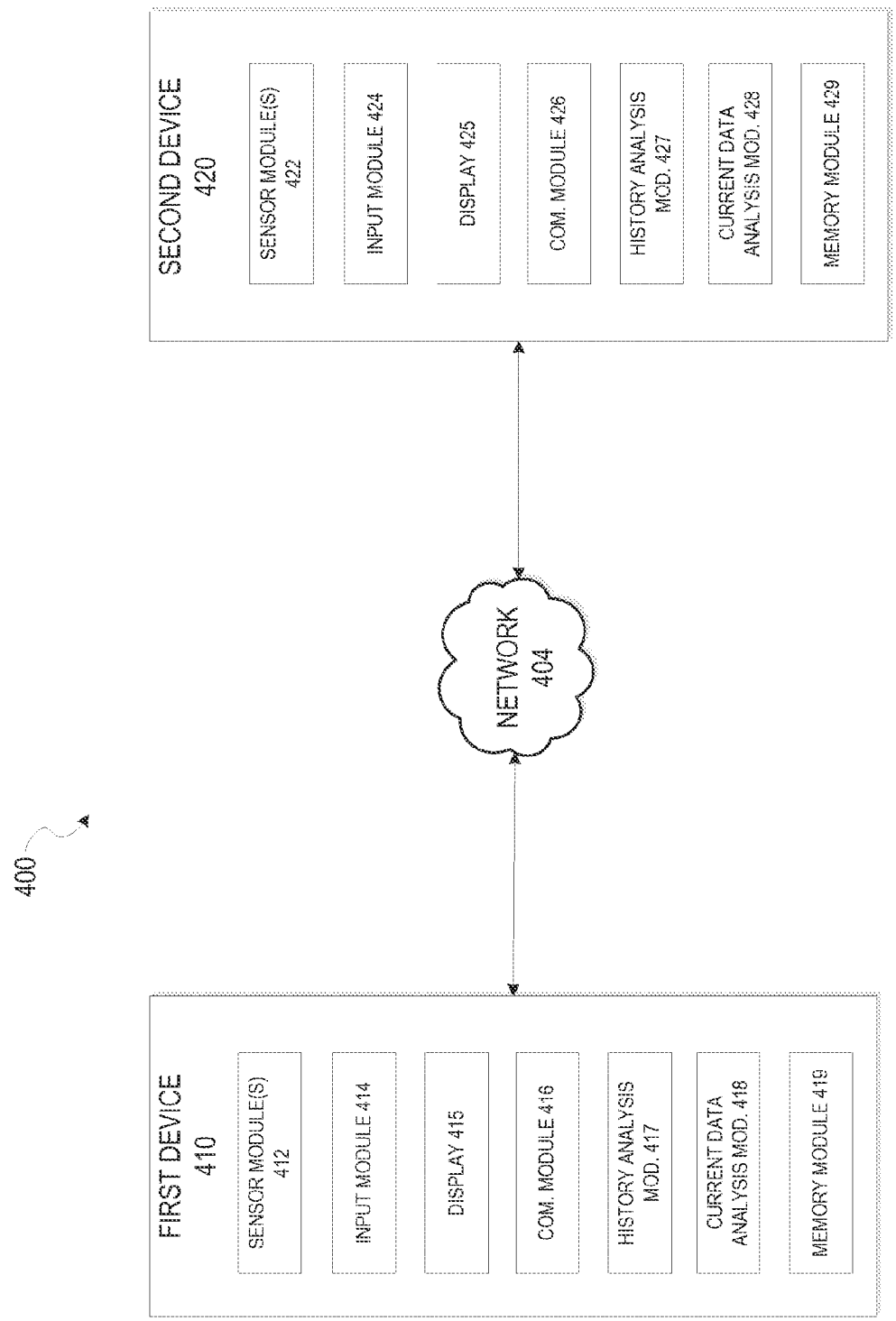
FIG. 4 illustrates another system for coordinated relationship wearables according to one example embodiment.

FIG. 4 is a block diagram illustrating another system for coordinating relationship wearables shown as system 400. System 400 includes a first device 410, a second device 120, and a network 404. In system 400, there is no analysis device similar to analysis device 130. Instead, analysis modules are implemented as part of both first device 410 and second device 420 in certain implementations of system 400, first device 410 and second device 420 may both be wearable devices such as wristbands, armbands, or other products with integrated electronic components. In other implementations, first device 410 and second device 420 may each be coupled to other wearable devices. For example, in one implementation, first device 410 and second device 420 may each be smart phone devices with both cellular communication modules and local wireless communication modules that connect to other wearable devices. Such an embodiment, system 400 may be similar to the system illustrated by FIG. 1B but without the analysis device 130.

The implementation of a system 400 enables first device 410 and second device 420 to implement methods for coordinating the first device 410 with a second device 420 as a coordination between relationship wearables. First device 410 is shown as including sensor modules 412, output module 414, display 415, communication module 416, history analysis module 417, current data analysis module 418, and memory module 419. Similarly, second device 420 is shown as including sensor modules 422, input module 424, display 425, medication module 426, history analysis module 427, history data analysis module 428, and memory module 429. In certain embodiments, first device 410 and second device fir 20 may each be different copies of the same device type. In other embodiments, first device 410 and second device 420 may be different types of devices such as mobile phone devices, laptop computers, desktop computers, tablet devices, tablet devices, or any other such computing device.

System 400 may implement any method described above for system 100, but system 400, one or both of history analysis module 417 and 427, and one or both of current data analysis module 418 and current data analysis module 428 may perform the analysis described above for history analysis module 134 entering data analysis module 138. Thus, in system 400, history analysis module 417 and history analysis module 427 may be identical to history analysis module 134. In other implementations, these modules may be altered to share analysis between them. This functionality may be divided in any possible way. Similarly, current data analysis module 418 and current data analysis module 428 may be identical copies of each other, and identical to history analysis module 134, or they may divide functionality described above for history analysis module 134 between them in any possible way.

Because system 400 does not include an independent analysis device 130 or any registration server, registration processes described above in the flowchart of FIG. 3 may be implemented through handshaking security communications between first device 410 and second device 420. This may involve shared passwords, application settings, or other such security and data sharing settings implemented as part of an application operating on each of first device 410 and second device 420 as described below in association with FIGS. 6A and 6B.

In alternate embodiments, a system may include any number of devices such as first device 410 and second device 420 with each device having their own history analysis modules and current data analysis modules, but with a separate registration server that manages privacy and identity interactions between devices in a system, and that assist in enabling direct communications between devices such as first device 410 and second device 420 which then enables the first device 410 and the second device 422 manage a coordination directly between the two devices.

Figure 5A:
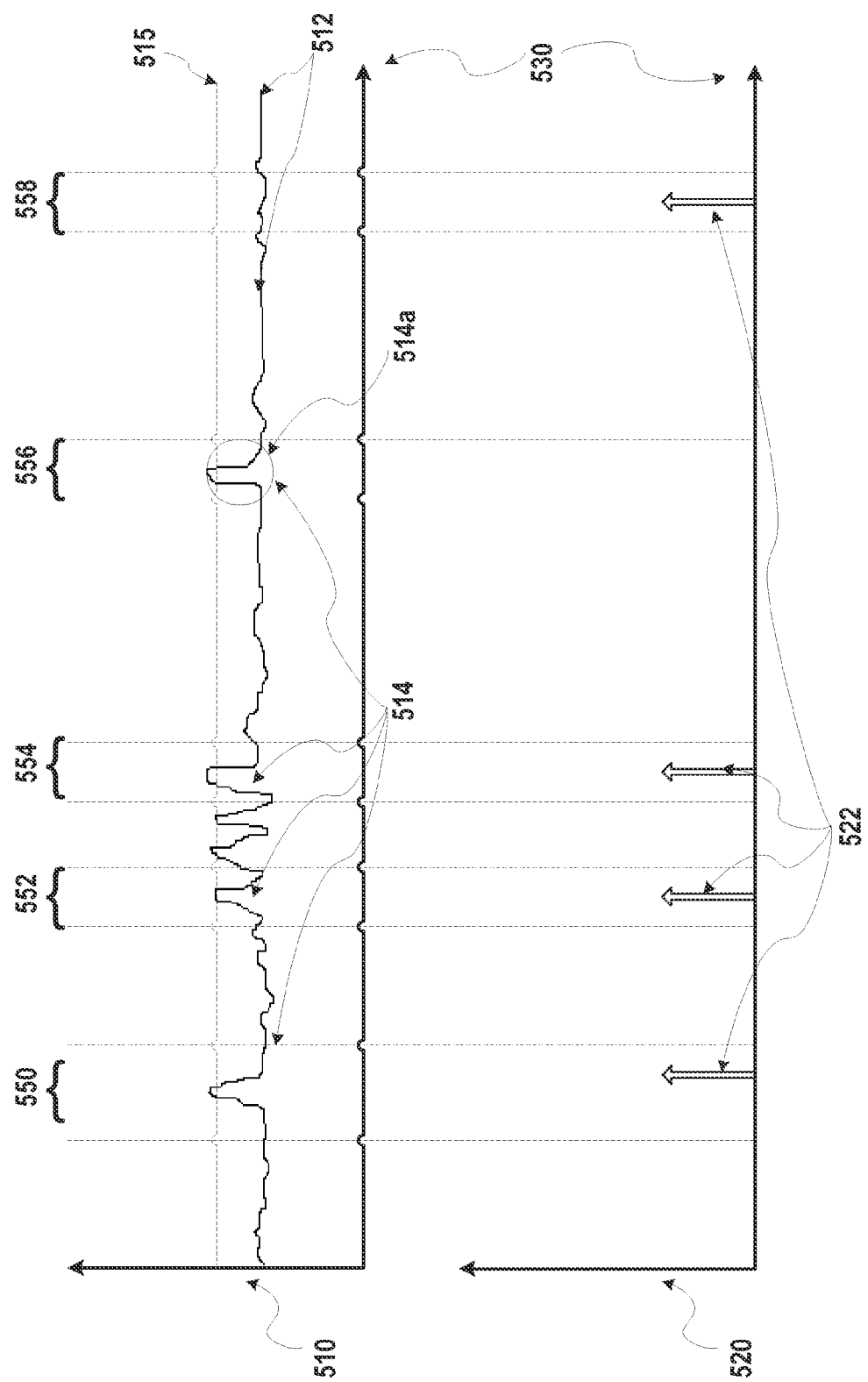
FIG. 5A illustrates one implementation of coordinated data between two devices according to some example embodiments for coordinating relationship wearables.
Figure 5B:
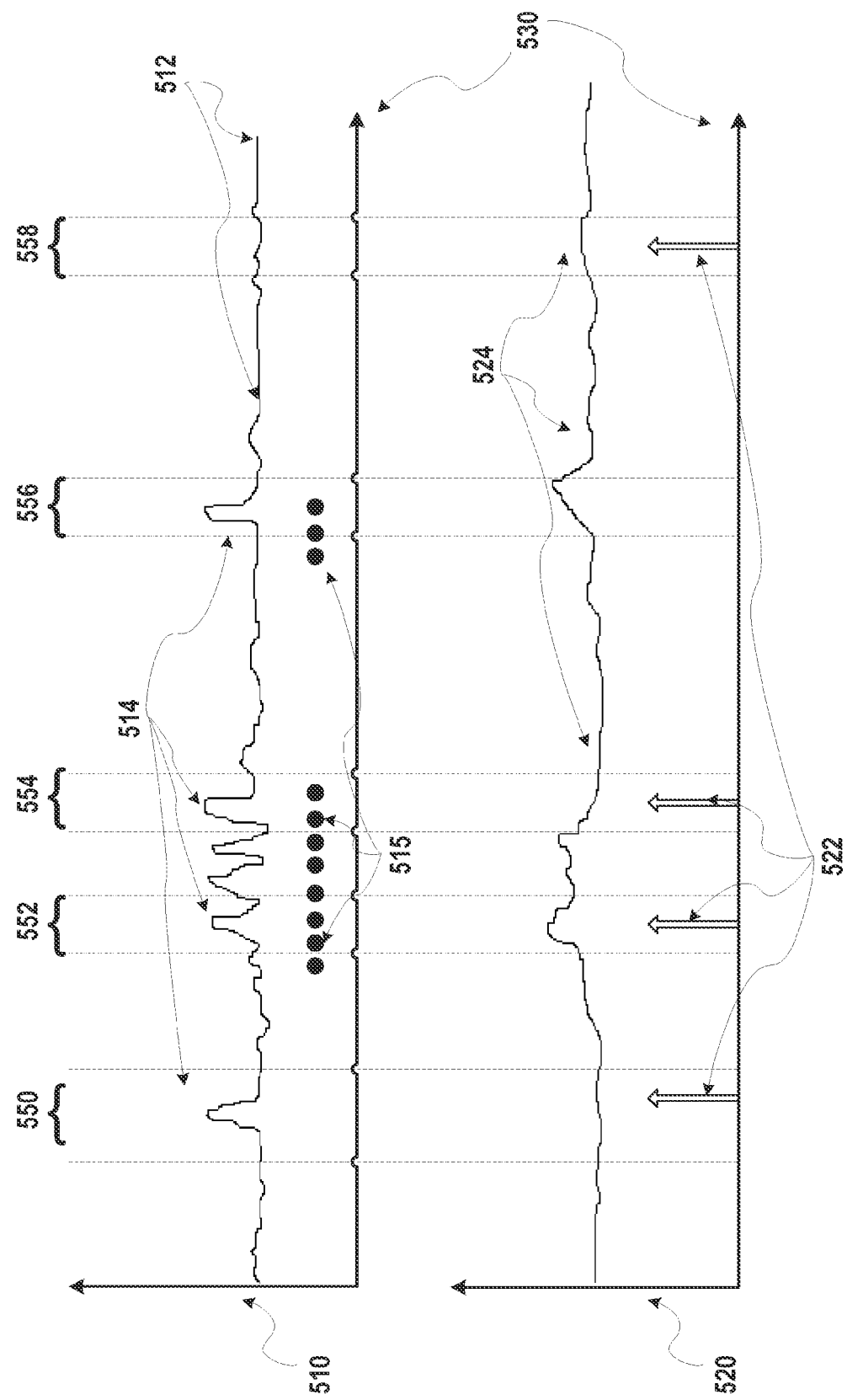
FIG. 5B illustrates another implementation of coordinated data between two devices according to an example embodiments for coordinating relationship wearables.

FIGS. 5A and 5B then illustrate aspects of coordinated data between two devices according to example embodiments for coordinating relationship wearables. In various embodiments, the data illustrated by FIGS. 5A and 5B may be used as history data comprising a first set of first device sensor data and a first set of second device data which may be analyzed by a history analysis module such as history analysis module 134, history analysis module 317, or history analysis module 327.

FIG. 5A shows data from two devices. Data from both devices is shown with a time axis 530. The upper set of data with of values axis 510 includes heart rate data 512. Such heart rate data 512 may be received from any device such as first wearable device 110. The lower set of data with values axis 520 includes user input data 522 which may be, for example, from an input device 124 of second device 120. In one embodiment, a user input data 522 may be an input from a user of a second device 120 which identifies a stress or attention level input by a user of the second device 120 used to describe user of the first device 110 or a coordinated relationship status. Such user input data 522 may be a simple binary yes/no value, or may be an input value on a scale. For example, the user input data 522 may be a value between one and 100. The example user input data 522 shown in FIG. 5A is a simple yes value associated with a particular time. This yes value may be a simple button on an application of second device 120, or may be part of an input user interface which requests a time associated with the user observation. Such an application would then process the input at the user interface to generate user input data 522.

Heart rate data 512 and user input data 522 may then be received at a history analysis module such as history analysis module 134. At history analysis module 134, heart rate data 512 and user input data 522 may be aligned on a common time axis as shown by time axis 530. The history analysis module may then apply pattern recognition algorithms or other analysis processes along with trigger thresholds to identify events. FIG. 5A shows trigger threshold element 515 which is a heart rate trigger threshold. Such a threshold may be an initial system trigger threshold which is used to identify repeated events, and which may then be modified or otherwise used to generate a trigger threshold or one or more elements of a trigger threshold which may be compared against a current data stream. FIG. 5A also shows events 550, 552, 554, 556, and 558. The history analysis module that receives are great data 512 and user input data 522 may analyze this data to identify events 550, 552, and 554 as repeated events that are part of a first coordinated relationship pattern. As part of this analysis, the user history analysis module may identify first repeated status values 514 within the heart rate data 512. The user history analysis module may additionally identify each instance of an input value of user input data 522 as a coordinated status value. The timing data received with each of these data streams may be used as timing data associated with the first repeated status values 514 and the first coordinated status values which are associated with input data 522. The history analysis module may then identify that repeated status values 514 and coordinated status values each occur during the time periods for events 550, 552, and 554.

History analysis module may use this identification of events 550, 552, and 554 to generate a set of coordinated relationship data. This coordinated relationship data may include at least information sufficient to generate a trigger threshold which would identify the repeated status values of heart rate data 512 when the set of coordinated relationship data is used by a current data analysis module 138 to analyze a later stream of data. When the subsequent stream of currents device data is received by a current data analysis module operating as part of the system, the current data analysis module may use the set of coordinated relationship data which includes the trigger threshold to identify an instance of data similar repeated status value 514 such as status value 514 a. Identification of such data in a current data stream is then used to initiate coordination communication.

As discussed above, data such as heart rate data 512 and user input data 522 may be used both as a first set of first device sensor data and the first set of second device data combined into historical data for use by a history analysis module and as for analysis by a current data analysis module. If such data is used by a current data analysis module, it may be passed to a history analysis module to update models, coordinated relationship patterns, trigger thresholds, and other such data that may be used as part of a set of coordinated relationship data. If such data is not used by a current data analysis module, it may simply be sent directly to a history analysis module for generation of initial sets of coordinated relationship data that establish initial coordinated relationship patterns and sets of coordinated relationship data which will later be used as part of an analysis by a current data analysis module.

While FIG. 5A shows a simple set of data comprising a single data type from first device and a single data type from the second device, FIG. 5B illustrates that data used by system may be more complex. For example, in addition to the elements shown by FIG. 5A, FIG. 5B additionally includes first device data 515 as well as second heart rate data 524 from a second device that may be the same device that generates user input data 522. For example in FIG. 1, second device 120 may generate both heart rate data 524 and user input data 522. In alternative implementations, user input data 522 may be received directly from input device 124 of second device 120, and heart rate data 524 may be received from a wearable device 121 wirelessly coupled to second device 120 which relays the heart rate data 524 to analysis module such as history analysis module 134 or current data analysis module 138.

First device data 515 may be any data associated with the user that generates heart rate data 514. First device data 515 may include social media status data scraped from a social media web page associated with a first user. First device data 515 may include facial image data associated with the first user. First device data 515 may include a first user status value derived from an expression recognition algorithm applied to facial image data associated with the first user. First device data may also be position data or a position value indicating whether a wearable user device with within a position geofence established as part of a trigger threshold, such as an "at home" geofence, a "commuting" geofence, or an "at work" geofence. In various embodiments, any or all of such data types may be included as part of a single set of historical data that includes a first set of first device sensor data from a first wearable device of a first user, and a second set of second device data from a second device of a second user, along with data from other sources. Similarly, any or all of such data types may be part of a current data stream received for analysis by a current data analysis module.

In another alternative implementation such as system 400 of FIG. 4, heart rate data 524 may be collected by sensors for 22 of second device 420 and communicated to history analysis module 427 or current data analysis module 428 as part of operation of second device 120. In such embodiments, user input data 522 may be received via input module 424 and similarly communicated to history analysis module 427 or current data analysis module 428. In such an embodiment, heart rate data and first device data 515 may be communicated from first device to a second device as part of history data or current data stream to be analyzed by history analysis module 427 or current data analysis module 428.

In additional similar embodiments operating using system 400, history analysis modules 417 and 427 may operate at the same time so that, for example, heart rate data 514 may be sent to both history analysis module 417 and history analysis module 427. History analysis module 417 and history analysis module 427 a then use the same input data to generate separate sets of coordinated relationship data which are also independently used by 418 and current data analysis module 428 receiving information from their respective history analysis modules. Such simultaneous independent operation may enable a first device to perform a first analysis and generate a first coordinated communication at the same time that a second device is performing a similar analysis that may or may not use different analysis procedures to generate a separate independent coordination communication. The coordination process for the relationship wearables may thus involve similar but separate coordination processes using the same sets of data from the coordinated devices.

FIG. 5B additionally shows the same events 550, 552, 554, 556, and 558. As described above, a set of history data may have multiple different trigger thresholds used to generate triggers which may be associated with different coordination communications. For example, a first trigger threshold may be associated only with heart rate data 514, a second trigger threshold may be associated both with heart rated a 514 and first device data 515, a third trigger threshold may be associated with heart rate data 514, first device data 515, heart rate data 524, and user input data 522. Additionally, a system may identify different coordinated relationship patterns within the same set of data using different combinations of such data by selecting different data types from among the available information that is part of a coordinated relationship between wearables.

Figure 6A:
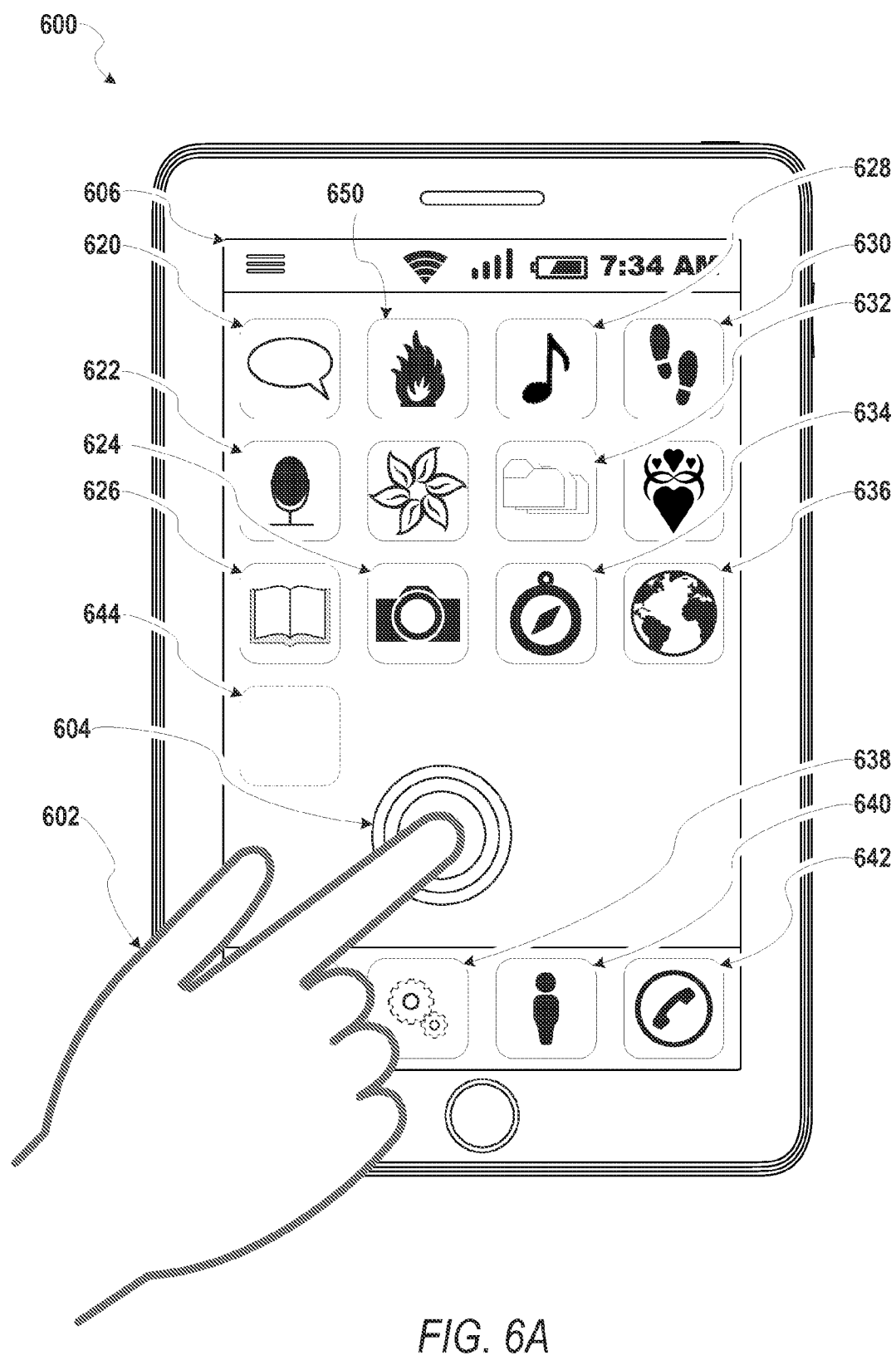
FIG. 6A depicts an example mobile device and mobile operating system interface, according to some example embodiments.
Figure 6B:
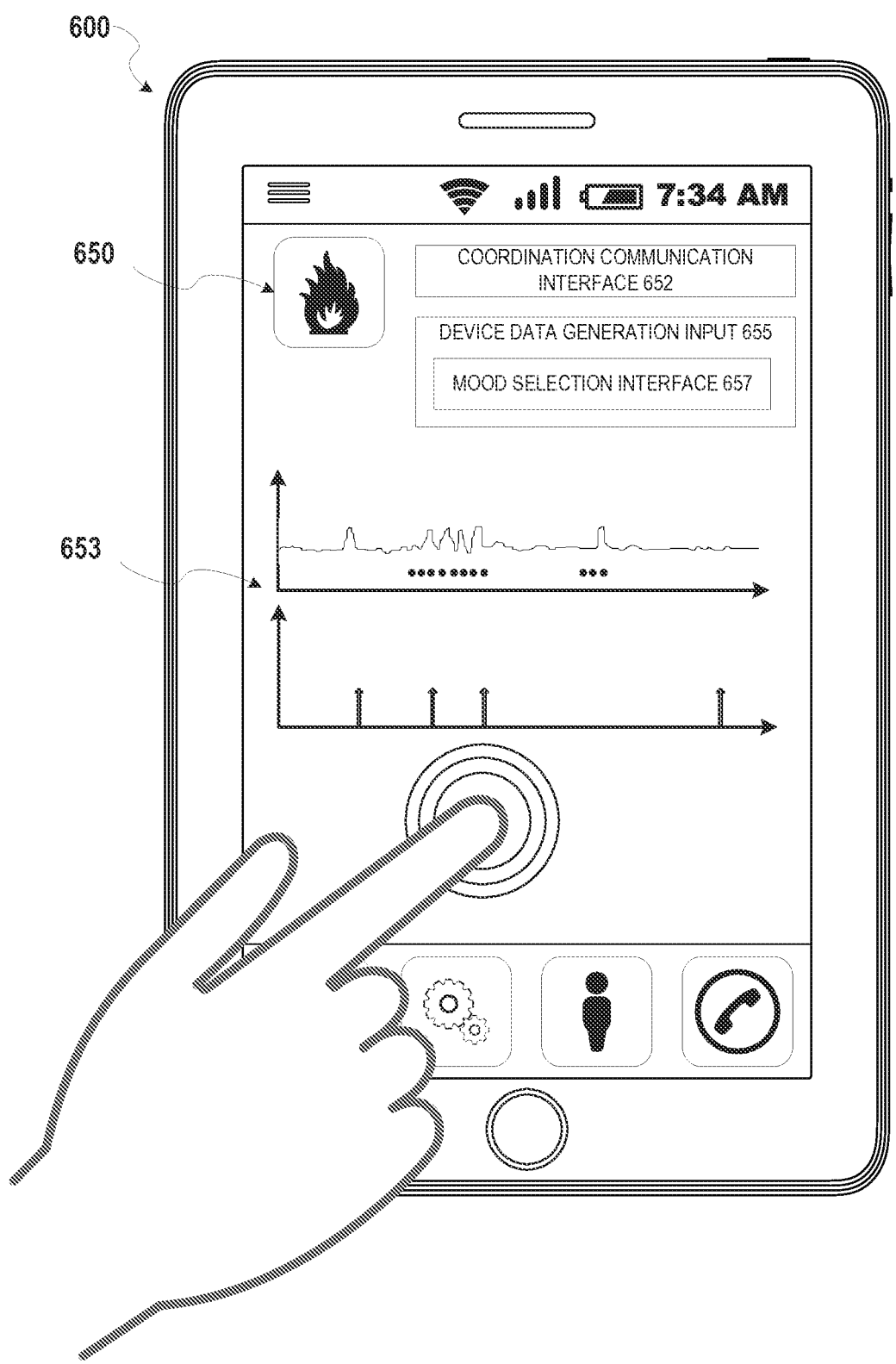
FIG. 6B depicts an example mobile device and mobile operating system interface, according to some example embodiments.

FIGS. 6A and 6B depict an example device and operating system interface, according to some example embodiments. In various embodiments, such an example mobile device 600 may be an implementation of any device described herein, including first wearable device 110, second device 120, first device 410, second device 420, first analysis device 130, or any other computing or networking device used as part of a system for coordinating relationship wearables. FIG. 6A illustrates an example device 600 that may be executing a mobile operating system (e.g., iOS™, Android™, Windows® Phone, or other mobile operating systems), according to example embodiments.

In one embodiment, the mobile device 600 may include a touch screen that may receive tactile information from a user 602. For instance, the user 602 may physically touch 604 the mobile device 600, and in response to the touch 604, the mobile device 600 may determine tactile information such as touch location, touch force, gesture motion, and on forth. In various example embodiments, the mobile device 600 may display home screen 606 (e.g., Springboard on iOS™) that the user 602 of the mobile device 600 may use to launch applications and otherwise manage the mobile device 600. In various example embodiments, the home screen 606 may provide status information such as battery life, connectivity, or other hardware status. The home screen 606 may also include a plurality of icons that may be activated to launch applications, for example, by touching 604 the area occupied by the icon. Similarly, other user interface elements may be activated by touching 604 an area occupied by a particular user interface element. In this manner, the user 602 may interact with the applications.

Many varieties of applications (also referred to as "apps") may be executing on the mobile device 600. The applications may include native applications (e.g., applications programmed in Objective-C running on iOS™ or applications programmed in Java running on Android™), mobile web applications (e.g., HTML5), or hybrid applications (e.g., a native shell application that launches an HTML5 session). In a specific example, the mobile device 600 may include a messaging app 620, audio recording app 622, a camera app 624, a book reader app 626, a media app 628, a fitness app 630, a file management app 632, a location app 634, a browser app 636, a settings app 638, a contacts app 640, a telephone call app 642, other apps (e.g., gaming apps, social networking apps, biometric monitoring apps), a third party app 644, and so forth.

Device 600 may particularly include a coordination application 650 that includes a history analysis module, a current data analysis module, a coordination communication module, or any other such systems for implementing coordination between relationship wearables described herein.

FIG. 6B illustrates one potential user interface that may be associated with a coordination application 650. Coordination application 650 may include a user interface including coordination communication interface 652 which may display a coordination communication along with any portion of a set of coordinated relationship data comprising a trigger or repeated status value that was used to initiate the coordination communication displayed on coordination communication interface 652. As discussed above, the coordination communication may simply list the repeated status value which was identified in the current data stream. The coordination communication may additionally list the trigger threshold which was used to identify the repeated status value. The coordination communication may also present a pre-generated message that is input to a system by a user as part of system registration or system selections, for example, as part of operation 266.

Coordination communication interface 652 may include a device data generation input 655 which may be used to generate relationship data. For example, device data generation input 655 may include a drop down menu with a list of "mood" options such as "happy," "stressed," "angry," "tired," or any other such options. A touch input on such a mood selection interface may be used to generate device data which is associated with a time-stamp of the time of selection, and used by the system as relationship data.

Coordination communication interface 652 may display graphs such as graphs 653 which may illustrate events and data such as the graphs illustrated by FIGS. 5A and 5B. Coordination communication interface 652 may also include statistical details about any coordinated relationship patterns between the devices associated with a coordination communication. This may include, for example, a statistical association between instances of the repeated status value identified by the trigger threshold and the occurrence of the event that is part of the coordinated relationship pattern along with any other content. If a coordination communication is associated with one tier of a trigger threshold associated with other similar trigger thresholds or tiers of a trigger threshold, the coordination communication interface 652 may also display any such data associated with other trigger thresholds, coordinated relationship patterns, or sets of coordinated relationship data that use data types or have any association with the data used to initiate the coordination communication displayed by coordination communication interface 652.

In additional alternative embodiments, relationship application 650 may include additional interfaces, user input interface, or other such interfaces as part of coordination relationship wearables as described herein. For example, application 650 may include an input interface for selecting additional data inputs from pre-generated lists of data options as part of an input module or input device 124. Application 650 may also include a user interface for inputting analysis parameters and communication parameters. Application 650 may also include user interface modules for preforming registration, device association, privacy selection, account relationship creation or association, or any other such process described herein.

Figure 7:
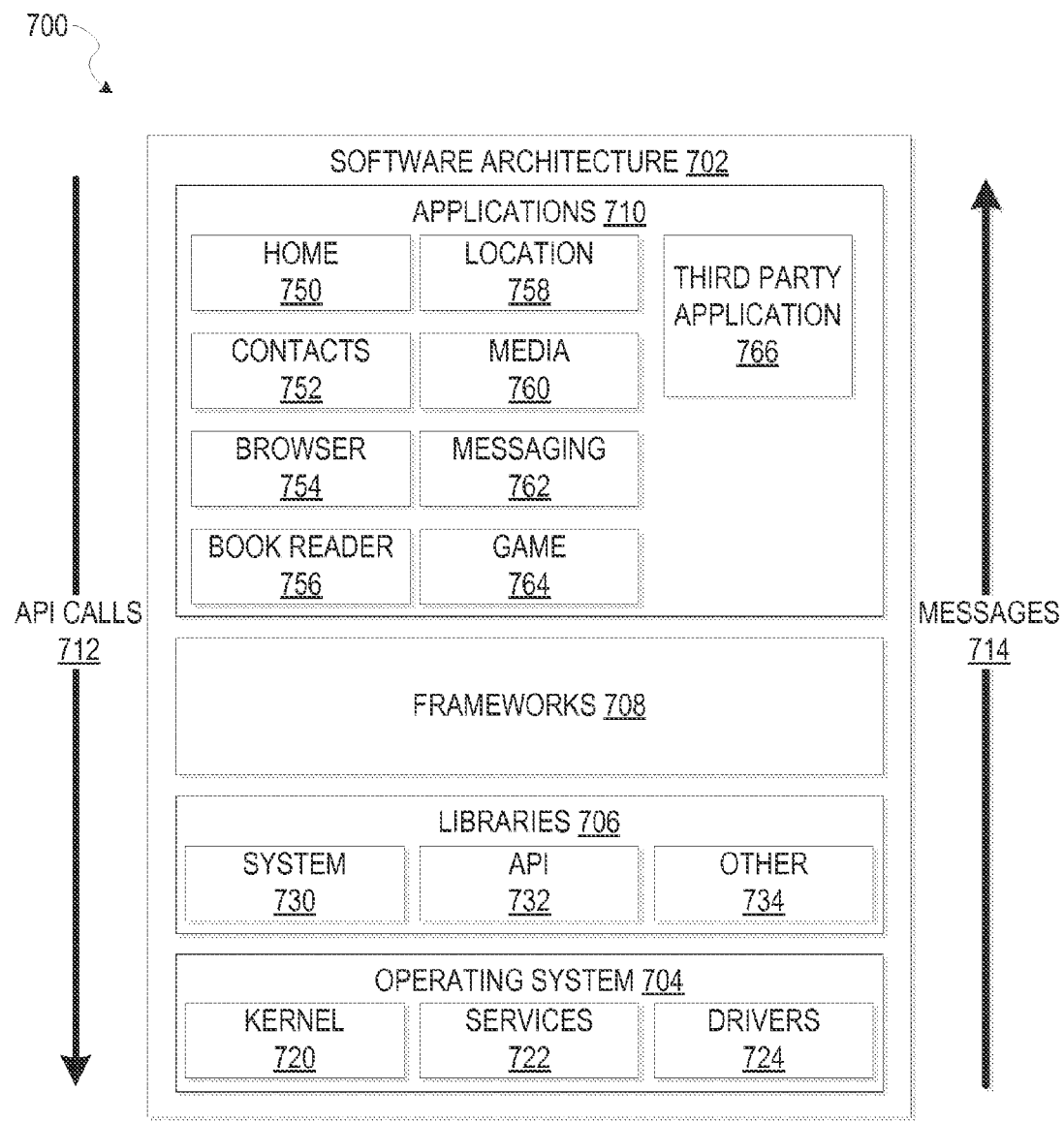
FIG. 7 is a block diagram illustrating an example of a software architecture that may be installed on a machine, according to some example embodiments.

FIG. 7 is a block diagram 700 illustrating an architecture of software 702 which may be installed on any one or more of the devices described herein, including mobile devices 180 and 600 which may operate a fitness application 630. FIG. 7 is merely a non-limiting example of a software architecture and it will be appreciated that many other architectures may be implemented to facilitate the functionality described herein. The software 702 may be executing on hardware such as machine 800 of FIG. 8 that includes processors 810, memory 830, and I/O components 850. In the example architecture of FIG. 7, the software 702 may be conceptualized as a stack of layers where each layer may provide particular functionality. For example, the software 702 may include layers such as an operating system 704, libraries 706, frameworks 708, and applications 710. Operationally, the applications 710 may invoke application programming interface (API) calls 712 through the software stack and receive messages 714 in response to the API calls 712.

The operating system 704 may manage hardware resources and provide common services. The operating system 704 may include, for example, a kernel 720, services 722, and drivers 724. The kernel 720 may act as an abstraction layer between the hardware and the other software layers. For example, the kernel 720 may be responsible for memory management, processor management (e.g., scheduling), component management, networking, security settings, and so on. The services 722 may provide other common services for the other software layers. The drivers 724 may be responsible for controlling or interfacing with the underlying hardware. For instance, the drivers 724 may include display drivers, camera drivers, Bluetooth® drivers, flash memory drivers, serial communication drivers (e.g., Universal Serial Bus (USB) drivers), Wi-Fi® drivers, audio drivers, power management drivers, and so forth.

The libraries 706 may provide a low-level common infrastructure that may be utilized by the applications 710. The libraries 706 may include system libraries 730 (e.g., C standard library) that may provide functions such as memory allocation functions, string manipulation functions, mathematic functions, and the like. In addition, the libraries 706 may include API libraries 732 such as media libraries (e.g., libraries 706 to support presentation and manipulation of various media format such as MPEG4, H.264, MP3, AAC, AMR, JPG), graphics libraries (e.g., an OpenGL framework that may be used to render 2D and 3D in graphic content on a display), database libraries (e.g., SQLite that may provide various relational database functions), web libraries (e.g., WebKit that may provide web browsing functionality), and the like. The libraries 706 may also include a wide variety of other libraries 734 to provide many other APIs to the applications 710.

The frameworks 708 may provide a high-level common infrastructure that may be utilized by the applications 710. For example, the frameworks 708 may provide various graphic user interface (GUI) functions, high-level resource management, high-level location services, and so forth. The frameworks 708 may provide a broad spectrum of other APIs that may be utilized by the applications 710, some of which may be specific to a particular operating system or platform.

The applications 710 include a home application 750, a contacts application 752, a browser application 754, a book reader application 756, a location application 758, a media application 760, a messaging application 762, a game application 764, and a broad assortment of other applications 710 such as third party application 766. In a specific example, the third party application 766 (e.g., an application developed using the Android™ or iOS™ software development kit (SDK) by an entity other than the vendor of the particular platform) may be mobile software running on a mobile operating system 704 such as iOS™, Android™, Windows® Phone, or other mobile operating systems. In this example, the third party application 766 may invoke the API calls 712 provided by the operating system 704 to facilitate functionality described herein. In various embodiments, these applications may interact with a fitness application 630 in various ways. For example, a messaging application 762 may be used for alerts or any communications with a waist measuring belt. A game application 764 may receive estimated waist values or other waist measurements as inputs to a game over time that may present a user with achievements based on waist measurements in conjunction with exercise inputs, heart rate inputs, or other such inputs.

Figure 8:
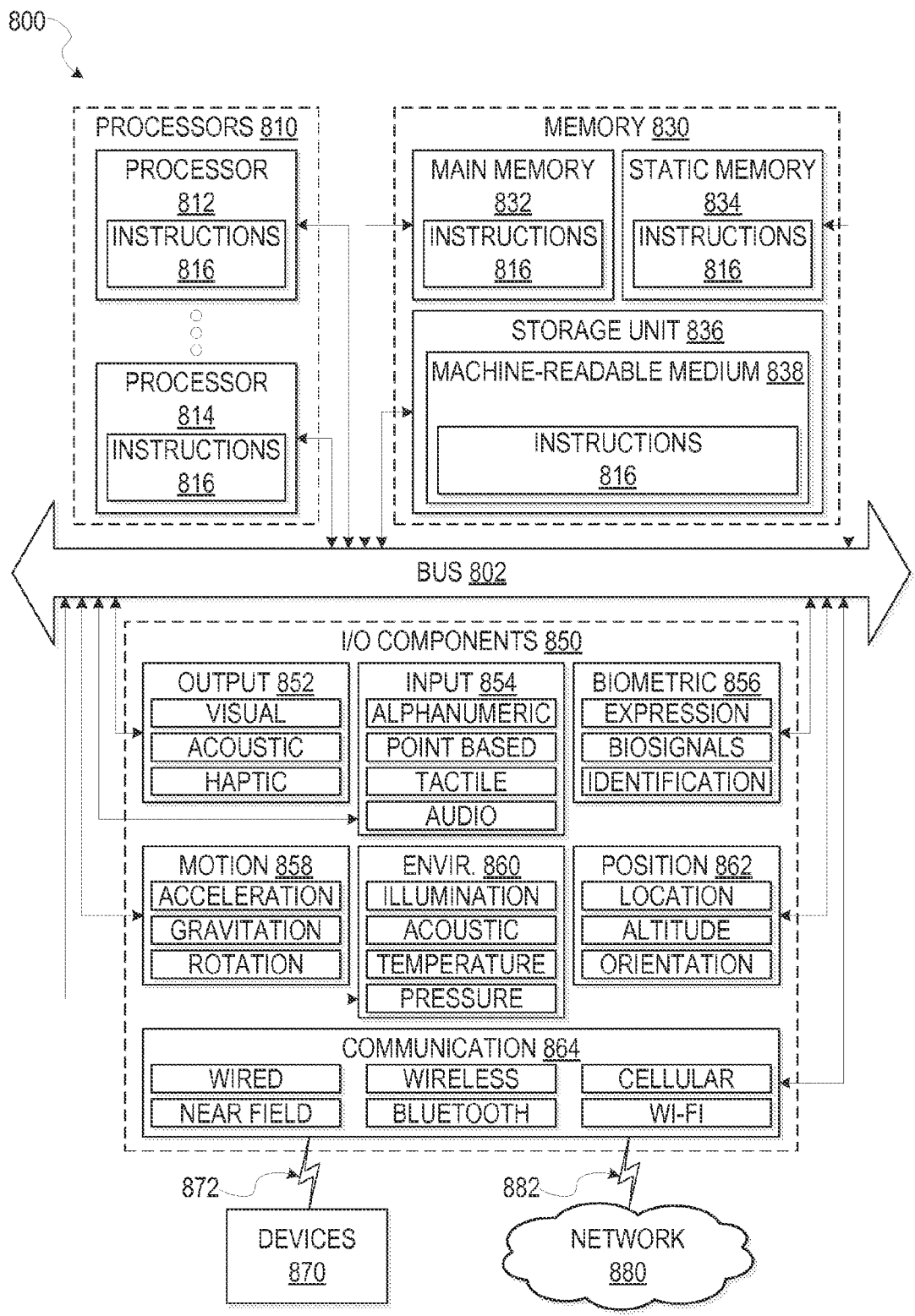
FIG. 8 illustrates a diagrammatic representation of a machine in the form of a computer system within which a set of instructions may be executed for causing the machine to perform any one or more of the methodologies discussed herein, according to an example embodiment.

FIG. 8 is a block diagram illustrating components of a machine 800, according to some example embodiments, able to read instructions from a machine-readable medium (e.g., a machine-readable storage medium) and perform any one or more of the methodologies discussed herein, including operation of a fitness application 630 that communicates with a waist measuring belt. Specifically, FIG. 8 shows a diagrammatic representation of the machine 800 in the example form of a computer system, within which instructions 816 (e.g., software, a program, an application, an applet, app, or other executable code) for causing the machine 800 to perform any one or more of the methodologies discussed herein may be executed. In alternative embodiments, the machine 800 operates as a standalone device or may be coupled (e.g., networked) to other machines. In a networked deployment, the machine 800 may operate in the capacity of a server machine or a client machine in a server-client network environment, or as a peer machine in a peer-to-peer (or distributed) network environment. The machine 800 may comprise, but not be limited to, a server computer, a client computer, a personal computer (PC), a tablet computer, a laptop computer, a netbook, a set-top box (STB), personal digital assistant (PDA), an entertainment media system, a cellular telephone, a smartphone, a mobile device 600, a wearable device (e.g., a smart watch), a smart home device (e.g., a smart appliance), other smart devices, a web appliance, a network router, a network switch, a network bridge, or any machine capable of executing the instructions 816, sequentially or otherwise, that specify actions to be taken by machine 800. Further, while only a single machine 800 is illustrated, the term "machine" shall also be taken to include a collection of machines 800 that individually or jointly execute the instructions 816 to perform any one or more of the methodologies discussed herein.

The machine 800 may include processors 810, memory 830, and I/O components 850, which may be configured to communicate with each other via a bus 802. In an example embodiment, the processors 810 (e.g., a central processing unit (CPU), a reduced instruction set computing (RISC) processor, a complex instruction set computing (CISC) processor, a graphics processing unit (GPU), digital signal processor (DSP), an application specific integrated circuit (ASIC), a radio-frequency integrated circuit (RFIC), another processor, or any suitable combination thereof) may include, for example, a processor 812 and a processor 814 that may execute the instructions 816. The term "processor" is intended to include multi-core processor that may comprise two or more independent processors also referred to as "cores") that may execute the instructions 816 contemporaneously. Although FIG. 8 shows multiple processors 810, the machine 800 may include a single processor 810 with a single core, a single processor 810 with multiple cores (e.g., a multi-core process), multiple processors 810 with a single core, multiple processors 810 with multiples cores, or any combination thereof.

The memory 830 may include a main memory 832, a static memory 834, and a storage unit 836 accessible to the processors 810 via the bus 802. The storage unit 836 may include a machine-readable medium 838 on which are stored the instructions 816 embodying any one or more of the methodologies or functions described herein. The instructions 816 may also reside, completely or at least partially, within the main memory 832, within the static memory 834, within at least one of the processors 810 (e.g., within the processor's cache memory), or any suitable combination thereof during execution thereof by the machine 800. Accordingly, the main memory 832, static memory 834, and the processors 810 may be considered machine-readable media 838.

As used herein, the term "memory" refers to a machine-readable medium 838 able to store data temporarily or permanently and may be taken to include, but not be limited to, random-access memory (RAM), read-only memory (ROM), buffer memory, flash memory, and cache memory. While the machine-readable medium 838 is shown in an example embodiment to be a single medium, the term "machine-readable medium" should be taken to include a single medium or multiple media (e.g., a centralized or distributed database, or associated caches and servers) able to store instructions 816. The term "machine-readable medium" shall also be taken to include any medium, or combination of multiple media, that is capable of storing instructions (e.g., instructions 816) for execution by a machine (e.g., machine 800), such that the instructions 816, when executed by one or more processors of the machine 800 (e.g., processors 810), cause the machine 800 to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" shall accordingly be taken to include, but not be limited to, one or more data repositories in the form of a solid-state memory (e.g., flash memory), an optical medium, a magnetic medium, other non-volatile memory (e.g., erasable programmable read-only memory (EPROM)), or any suitable combination thereof. The term "machine-readable medium" specifically excludes non-statutory signals per se. Any such memory may be included as part of any device such as first wearable device 110, second device 120, second wearable devices 121, first device 410, second device 420, independent networked sensor modules, or any other such devices or modules described herein.

The I/O components 850 may include a wide variety of components to receive input, provide output, produce output, transmit information, exchange information, capture measurements, and so on. It will be appreciated that the I/O components 850 may include many other components that are not shown in FIG. 8. The I/O components 850 are grouped according to functionality merely for simplifying the following discussion, and the grouping is in no way limiting. In various example embodiments, the I/O components 850 may include output components 852 and input components 854. The output components 852 may include visual components (e.g., a display such as a plasma display panel (PDP), light emitting diode (LED) display, a liquid crystal display (LCD), a projector, or a cathode ray tube (CRT)), acoustic components (e.g., speakers), haptic components (e.g., a vibratory motor), other signal generators, and so forth. The input components 854 may include alphanumeric input components (e.g., a keyboard, a touch screen configured to receive alphanumeric input, a photo-optical keyboard, or other alphanumeric input components), point based input components (e.g., a mouse, a touchpad, a trackball, a joystick, a motion sensor, or other pointing instruments), tactile input components (e.g., a physical button, a touch screen that provides location and force of touches or touch gestures, or other tactile input components), audio input components (e.g., a microphone), and the like.

In further example embodiments, the I/O components 850 may include biometric components 856, motion components 858, environmental components 860, or position components 862 among a wide array of other components. For example, the biometric components 856 may include components to detect expressions (e.g., hand expressions, facial expressions, vocal expressions, body gestures, or eye tracking), measure biosignals e.g., blood pressure, heart rate, body temperature, perspiration, or brain waves), identify a person (e.g., voice identification, retinal identification, facial identification, fingerprint identification, or electroencephalogram based identification), and the like. The motion components 858 may include acceleration sensor components (e.g., accelerometer), gravitation sensor components, rotation sensor components (e.g., gyroscope), and so forth. The environmental components 860 may include, for example, illumination sensor components (e.g., photometer), temperature sensor components (e.g., one or more thermometers that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detect concentrations of hazardous gases for safety or to measure pollutants in the atmosphere), or other components that may provide indications, measurements, or signals corresponding to a surrounding physical environment. The position components 862 may include location sensor components (e.g., a Global Positioning System (GPS) receiver component), altitude sensor components (e.g., altimeters or barometers that detect air pressure from which attitude may be derived), orientation sensor components (e.g., magnetometers), and the like.

Communication may be implemented using a wide variety of technologies. The I/O components 850 may include communication components 864 operable to couple the machine 800 to a network 880 or devices 870 via coupling 882 and coupling 872 respectively. For example, the communication components 864 may include a network interface component or other suitable device to interface with the network 880. In further examples, communication components 864 may include wired communication components, wireless communication components, cellular communication components, near field communication (NEC) components, Bluetooth® components (e.g., Bluetooth® Low Energy), Wi-Fi® components, and other communication components 864 to provide communication via other modalities. The devices 870 may be another machine 800 or any of a wide variety of peripheral devices (e.g., a peripheral device coupled via a Universal Serial Bus (USB)).

Moreover, the communication components 864 may detect identifiers or include components operable to detect identifiers. For example, the communication components 864 may include radio frequency identification (RFID) tag reader components, NEC smart tag detection components, optical reader components (e.g., an optical sensor to detect one-dimensional bar codes such as Universal Product Code (UPC) bar code, multi-dimensional bar codes such as Quick Response (QR) codes, Aztec code, Data Matrix, Dataglyph, MaxiCode, PDF417, Ultra Code, UCC RSS-2D bar codes, and other optical codes), or acoustic detection components (e.g., microphones to identify tagged audio signals). In addition, a variety of information may be derived via the communication components 864, such as location via Internet Protocol (IP) geo-location, location via Wi-Fi® signal triangulation, location via detecting an NFC beacon signal that may indicate a particular location, and so forth. In various embodiments, aspects of input devices 114, 124, 414, 424 communication module 116, 126, 132, 416, and 426 may be similar to different I/O components described above.

The instructions 816 may be transmitted or received over the network 880 using a transmission medium via a network interface device (e.g., a network interface component included in the communication components 864) and utilizing any one of a number of well-known transfer protocols (e.g., hypertext transfer protocol (HTTP)). Similarly, the instructions 816 may be transmitted or received using a transmission medium via the coupling 872 (e.g., a peer-to-peer coupling) to devices 870. The term "transmission medium" shall be taken to include any intangible medium that is capable of storing, encoding, or carrying instructions 816 for execution by the machine 800, and includes digital or analog communications signals or other intangible media to facilitate communication of such software.

Furthermore, the machine-readable medium 838 is non-transitory (in other words, not having any transitory signals) in that it does not embody a propagating signal. However, labeling the machine-readable medium 838 "non-transitory" should not be construed to mean that the medium is incapable of movement; the medium should be considered as being transportable from one physical location to another.

Additionally, since the machine-readable medium 838 is tangible, the medium may be considered to be a machine-readable device.

Additionally, various networks such as 104, 404, and 880 are described herein. Such networks represent an architecture for communication between devices such as any wearable device described herein as well mobile devices, server computers, or any other such computing devices. Any such devices may include applications or portions of applications as described herein.

Devices and network components operating as part of network 880, 104 and 404 may include any access point hardware, networking hardware, or communication device described herein which may be used to relay information between devices.

In various example embodiments, one or more portions of the network 104 or 404, or 880 may be an ad hoc network, an intranet, an extranet, a virtual private network (VPN), a local area network (LAN), a wireless LAN (WLAN), a wide area network (WAN), a wireless WAN (WWAN), a metropolitan area network (MAN), the Internet, a portion of the Internet, a portion of the public switched telephone network (PSTN), a plain old telephone service (POTS) network, a cellular telephone network, a wireless network, a Wi-Fi® network, another type of network, or a combination of two or more such networks. For example, the network 880 or a portion of the network 880 may include a wireless or cellular network and the coupling 882 may be a Code Division Multiple Access (CDMA) connection, a Global System for Mobile communications (GSM) connection, or another type of cellular or wireless coupling. In this example, the coupling 882 may implement any of a variety of types of data transfer technology, such as Single Carrier Radio Transmission Technology (1xRTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard-setting organizations, other long range protocols, or other data transfer technology.

Certain embodiments are described herein as including logic or a number of components, modules, or mechanisms. Modules may constitute either software modules (e.g., code embodied on a machine-readable medium or in a transmission signal) or hardware modules. A "hardware module" is a tangible unit capable of performing certain operations and may be configured or arranged in a certain physical manner. In various example embodiments, one or more computer systems (e.g., a standalone computer system, a client computer system, or a server computer system) or one or more hardware modules of a computer system (e.g., a processor or a group of processors) may be configured by software (e.g., an application or application portion) as a hardware module that operates to perform certain operations as described herein.

In some embodiments, a hardware module may be implemented mechanically, electronically, or any suitable combination thereof. For example, a hardware module may include dedicated circuitry or logic that is permanently configured to perform certain operations. For example, a hardware module may be a special-purpose processor, such as a field-programmable gate array (FPGA) or an application specific integrated circuit (ASIC). A hardware module may also include programmable logic or circuitry that is temporarily configured by software to perform certain operations. For example, a hardware module may include software encompassed within a general-purpose processor or other programmable processor. It will be appreciated that the decision to implement a hardware module mechanically, in dedicated and permanently configured circuitry, or in temporarily configured circuitry (e.g., configured by software) may be driven by cost and time considerations.

Accordingly, the phrase "hardware module" should be understood to encompass a tangible entity, be that an entity that is physically constructed, permanently configured (e.g., hardwired), or temporarily configured (e.g., programmed) to operate in a certain manner or to perform certain operations described herein. As used herein, "hardware-implemented module" refers to a hardware module. Considering embodiments in which hardware modules are temporarily configured (e.g., programmed), each of the hardware modules need not be configured or instantiated at any one instance in time. For example, where a hardware module comprises a general-purpose processor configured by software to become a special-purpose processor, the general-purpose processor may be configured as respectively different special-purpose processors (e.g., comprising different hardware modules) at different times. Software may accordingly configure, a particular processor or processors, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple hardware modules exist contemporaneously, communications may be achieved through signal transmission (e.g., over appropriate circuits and buses) between or among two or more of the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions described herein. As used herein, "processor-implemented module" refers to a hardware module implemented using one or more processors.

Similarly, the methods described herein may be at least partially processor-implemented, with a particular processor or processors being an example of hardware. For example, at least some of the operations of a method may be performed by one or more processors or processor-implemented modules. Moreover, the one or more processors may also operate to support performance of the relevant operations in a "cloud computing" environment or as a a "software as a service" (SaaS). For example, at least some of the operations may be performed by a group of computers (as examples of machines including processors), with these operations being accessible via a network 904 (e.g., the Internet) and via one or more appropriate interfaces (e.g., an application program interface (API)).

The performance of certain of the operations may be distributed among the processors, not only residing within a single machine, but deployed across a number of machines. In some example embodiments, the processors or processor-implemented modules may be located in a single geographic location (e.g., within a home environment, an office environment, or a server farm). In other example embodiments, the processors or processor-implemented modules may be distributed across a number of geographic locations.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Although an overview of the inventive subject matter has been described with reference to specific example embodiments, various modifications and changes may be made to these embodiments without departing from the broader scope of embodiments of the present disclosure. Such embodiments of the inventive subject matter may be referred to herein, individually or collectively, by the term "invention" merely for convenience and without intending to voluntarily limit the scope of this application to any single disclosure or inventive concept if more than one is, in fact, disclosed.

The embodiments illustrated herein are described in sufficient detail to enable those skilled in the art to practice the teachings disclosed. Other embodiments may be used and derived therefrom, such that structural and logical substitutions and changes may be made without departing from the scope of this disclosure. The Detailed Description, therefore, is not to be taken in a limiting sense, and the scope of various embodiments is defined only by the appended along with the full range of equivalents to which such claims are entitled.

As used herein, the term "or" may be construed in either an inclusive or exclusive sense. Moreover, plural instances may be provided for resources, operations, or structures described herein as a single instance. Additionally, boundaries between various resources, operations, modules, engines, and data stores are somewhat arbitrary, and particular operations are illustrated in a context of specific illustrative configurations. Other allocations of functionality are envisioned and may fall within a scope of various embodiments of the present disclosure. In general, structures and functionality presented as separate resources in the example configurations may be implemented as a combined structure or resource. Similarly, structures and functionality presented as a single resource may be implemented as separate resources. These and other variations, modifications, additions, and improvements fall within a scope of embodiments of the present disclosure as represented by the appended claims. The specification and drawings are, accordingly, to be regarded in an illustrative rather than a restrictive sense.

What is claimed is:

1. A system comprising:
   a first analysis module to:
   receive a first set of first device sensor data from a first wearable device of a first user, and a first set of second device data from a second device of a second user;
   identify a first coordinated relationship pattern comprising a plurality of events, each event of the plurality of events being associated with a first repeated status value within the first set of first device sensor data, a first coordinated status value within the first set of second device data, and a temporal association between the first repeated status value and the first coordinated status value;
   generate a trigger threshold associated with at least the first repeated status value;
   a first communication module communicatively coupled to the first analysis module, the first communication module to receive at least a portion of a first current data stream from the first wearable device;
   a second analysis module communicatively coupled to the first communication module, the second analysis module to analyze the first current data stream using the trigger threshold and to initiate a coordination communication to the second device communicating when the trigger threshold is met by a portion of the first current data stream; and
   a server computer, wherein the server computer comprises the first analysis module, and wherein the server computer is communicatively coupled to the first wearable device via a first mobile device and a wide area network.

2. The system of claim 1 wherein the first set of first device sensor data comprises a first set of heart rate measurements.

3. The system of claim 2 wherein the first set of first device sensor data further comprises a set of motion measurements from an accelerometer of the first wearable device.

4. The system of claim 3 wherein the first repeated status value comprises:
   a first heart rate measurement above a first heart rate threshold; and
   a non-exercise state value derived from at least a portion of the set of motion measurements in a first time period associated with the first heart rate measurement.

5. The system of claim 4 wherein the first coordinated status value comprises a set of second user inputs to a second device input module of the second device, wherein the set of second user inputs comprise a first mood category value input selected from a plurality of mood category values; and
   a time value, wherein the time value is within the first time period.

6. The system of claim 4 wherein the first set of second device data comprises a second set of heart rate measurements from a second device heart rate sensor; and
   wherein the first coordinated status value comprises a second heart rate measurement of the second set of heart rate measurements above a second threshold during the first time period.

7. The system of claim 1 further comprising a first mobile device, wherein the first mobile device comprises the first analysis module, the first communication module, and the second analysis module.

8. The system of 7 wherein the first mobile device further comprises the first wearable device.

9. The system of claim 1 wherein the second device comprises the first communication module and the second analysis module.

10. The system of claim 9 wherein the second device further comprises an alert module to present, on an output module of the second device, an alert and a coordinated relationship message associated with the first coordinated relationship pattern and the first coordinated status value.

11. The system of claim 1 wherein the server computer further comprises:
the first communication module and the second analysis module; and
a registration module that:
receives a first user registration for a first relationship account that associates one or more first account devices comprising the first wearable device with the first relationship account;
receives a second user registration for a second relationship account that associates one or more second account devices comprising the second device with the second relationship account;
receives a privacy communication from the one or more devices that associates the second relationship account with the first relationship account; and
receives one or more analysis settings from the one or more second account devices.

12. A method comprising:
receiving, at a first analysis module, a first set of first device sensor data from a first wearable device of a first user, and a first set of second device data from a second device of a second user;
identifying, by the first analysis module a first coordinated relationship pattern comprising a plurality of events, each event of the plurality of events being associated with a first repeated status value within the first set of first device sensor data, a first coordinated status value within the first set of second device data, and timing data associated with the first repeated status value and the first coordinated status value;
generating, from the first coordinated relationship pattern, a set of coordinated relationship data comprising a trigger threshold derived from at least the first repeated status value;
receiving, at a first communication module communicatively coupled to the first analysis module, at least a portion of a first current data stream from the first wearable device;
analyzing, by a second analysis module communicatively coupled to the first communication module, the first current data stream to determine when the trigger threshold is met by at least a portion of the first current data stream; and
initiating a coordination communication to the second device where trigger threshold is met by the first current data stream.

13. The method of claim 12 wherein the first set of first device sensor data comprises a first set of global positioning system (GPS) coordinates, wherein the first set of second device data comprises a second set of GPS coordinates.

14. The method of claim 12 wherein the first set of first device sensor data comprises a plurality of images of a face;
wherein the first analysis module analyzes each image of the plurality of images of the face to determine an identity and a facial expression value for each of the plurality of images of the face; and
wherein the first repeated status value comprises the facial expression value associated for images associated with the plurality of events.

15. The method of claim 12 further comprising:
receiving, at the first analysis module, a first set of third device sensor data from a second wearable device of the first user; and
receiving a current data communication from the second wearable device concurrently with the current data stream;
wherein each event of the plurality of events is further associated with a second repeated status value within the first set of the third device sensor data;
wherein the set of coordinated relationship data further comprises the second repeated status value; and
wherein the coordination communication is additionally communicated in response to an identification of the second repeated status value in the current data communication by the second analysis module.

16. The method of claim 12 further comprising:
receiving, from the second device, a set of threshold criteria for the first repeated status value;
wherein the first analysis module identifies the first repeated status value using the set of threshold criteria.

17. A non-transitory machine readable medium comprising machine readable instructions that, when executed by a processor coupled to the medium cause a device to:
receive a first set of first device sensor data from a first wearable device of a first user, and a first set of second device data from a second device of a second user;
identify, by the first analysis module a first coordinated relationship pattern comprising a plurality of events, each event of the plurality of events being associated with a first repeated status value within the first set of first device sensor data, a first coordinated status value within the first set of second device data, and a timing data associated with the first repeated status value and the first coordinated status value;
generate, from the first coordinated relationship pattern, a set of coordinated relationship data comprising a trigger threshold derived from at least the first repeated status value;
receive, at a first communication module communicatively coupled to the first analysis module, at least a portion of a first current data stream from the first wearable device;
analyze, by a second analysis module communicatively coupled to the first communication module, the first current data stream to determine when the trigger threshold is met by at least a portion of the first current data stream; and
initiate a coordination communication to the second device when the trigger threshold is met by the first current data stream.

18. The non-transitory machine readable medium of claim 17 wherein the first set of first device sensor data comprises a first set of global positioning system (GPS) coordinates, wherein the first set of second device data comprises a second set of GPS coordinates;
wherein the first set of first device sensor data comprises a plurality of images of a face; and
wherein the first analysis module analyzes each image of the plurality of images of the face to determine an identity and a facial expression value for each of the plurality of images of the face; and wherein the first repeated status value comprises the facial expression value associated for images associated with the plurality of events.

19. The non-transitory machine readable medium of claim 17 wherein the instructions further cause the device to:
receive, at the first analysis module, a first set of third device sensor data from a second wearable device of the first user; and
receive a current data communication from the second wearable device concurrently with the current data stream;
wherein each event of the plurality of events is further associated with a second repeated status value within the first set of the third device sensor data;
wherein the set of coordinated relationship data further comprises the second repeated status value; and
wherein the coordination communication is additionally communicated in response to an identification of the second repeated status value in the current data communication by the second analysis module.

20. The non-transitory machine readable medium of claim 17 wherein the instructions further cause the device to:
receive, from the second device, a set of threshold criteria for the first repeated status value,
wherein the first analysis module identifies the first repeated status value using the set of threshold criteria.

* * * * *

UNITED STATES PATENT AND TRADEMARK OFFICE
CERTIFICATE OF CORRECTION

PATENT NO. : 9,901,301 B2
APPLICATION NO. : 14/569518
DATED : February 27, 2018
INVENTOR(S) : Jennifer T. Brenner et al.

Page 1 of 1

It is certified that error appears in the above-identified patent and that said Letters Patent is hereby corrected as shown below:

On the Title Page

Item (57), in Column 2, in "Abstract", Line 8, delete "patters" and insert -- patterns --, therefor.

In the Claims

In Column 27, Line 1, in Claim 8, after "of" insert -- claim --.

In Column 27, Line 56, in Claim 12, delete "where" and insert -- when the --, therefor.

In Column 29, Line 24, in Claim 20, delete "value," and insert -- value; --, therefor.

Signed and Sealed this
Twenty-ninth Day of May, 2018

Andrei Iancu
*Director of the United States Patent and Trademark Office*